United States Patent [19]

Bagley et al.

[11] Patent Number: 5,053,411
[45] Date of Patent: Oct. 1, 1991

[54] N-ARYL-N-(4-(1-HETEROCYCLICALKYL)-PIPERIDINYL)AMIDES AND PHARMACEUTICAL COMPOSITIONS AND METHODS EMPLOYING SUCH COMPOUNDS

[75] Inventors: Jerome R. Bagley, North Plainfield, N.J.; Nhora L. Lalinde, West Nyack, N.Y.; Bao-Shan Huang, Edison; H. Kenneth Spencer, Chatham, both of N.J.

[73] Assignee: Anaquest, Inc., Murray Hill, N.J.

[21] Appl. No.: 341,094

[22] Filed: Apr. 20, 1989

[51] Int. Cl.$^5$ .......... A61K 31/505; A61K 31/52; C07D 405/02; C07D 239/72
[52] U.S. Cl. .......... 514/259; 514/262; 514/265; 514/266; 514/326; 514/316; 514/320; 514/321; 514/322; 544/260; 544/211; 544/216; 544/217; 544/285; 544/280; 544/284; 544/289; 544/290; 544/291; 544/292; 544/293; 546/196; 546/198; 546/199; 546/201; 546/202; 546/208; 546/212; 546/213
[58] Field of Search .......... 548/255, 266; 546/210; 514/326, 265, 259, 260, 265, 262, 266; 544/277, 283, 285, 287, 266, 271, 276, 286, 289, 290-293

[56] References Cited
U.S. PATENT DOCUMENTS 4,584,303 4/1986 Huang et al. .......... 546/210

4,791,120 12/1988 Lin et al. .......... 514/326

OTHER PUBLICATIONS

Colapret et al., J. Med. Chem., vol. 32, 968-974 (1989).

Primary Examiner—Mukund J. Shah
Assistant Examiner—Jyothsna Venkat
Attorney, Agent, or Firm—R. Hain Swope; Larry R. Cassett

[57] ABSTRACT

This invention pertains to novel substituted N/aryl-N-[4-(1-heterocyclicalkyl)piperidinyl]amides useful as analgesics, and methods of administering analgesia, which comprises the systemic administration to mammals of such compounds, and pharmaceutical compositions containing such compounds, wherein the novel compounds have the general formula:

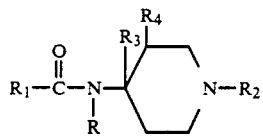

including optically active isomeric forms, and the pharmaceutically acceptable acid addition salts thereof, wherein R, $R_1$, $R_2$, $R_3$ and $R_4$ are defined in the disclosure.

30 Claims, No Drawings

N-ARYL-N-(4-(1-HETEROCYCLICALKYL)-PIPERIDINYL)AMIDES AND PHARMACEUTICAL COMPOSITIONS AND METHODS EMPLOYING SUCH COMPOUNDS

The present invention relates to substituted N-aryl-N-[4-(1-heterocyclicalkyl)piperidinyl]amides, and pharmaceutical compositions and methods employing such compounds.

BACKGROUND OF THE INVENTION

A number of patents disclose certain N-aryl-N-[4-(1-heterocyclicalkyl)piperidinyl]amides having therapeutic activity. For example, U.S. Pat. No. 3,998,834, issued to Janssen et al. and assigned to Janssen Pharmaceuticals N. V., discloses certain N-phenyl-N-[4-(1-heterocyclic)piperidinyl]amide compounds useful as analgesics. U.S. Pat. No. 4,584,303, issued to Huang et al. and assigned to The BOC Group, Inc., also discloses certain N-phenyl-N-[4-(1-heterocyclic)piperidinyl]amide compounds useful as analgesics.

SUMMARY OF THE INVENTION

This invention pertains to novel substituted N-aryl-N-[4-(1-heterocyclicalkyl)piperidinyl]amides useful as analgesics, and methods of administering analgesia, which comprises the systemic administration to mammals of such compounds, and pharmaceutical compositions containing such compounds, wherein the novel compounds have the general formula:

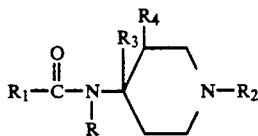

including optically active isomeric forms, and the pharmaceutically acceptable acid addition salts thereof, wherein:

R is an aryl group selected from the group consisting of Phenyl and substituted Phenyl, wherein the substituent groups on the phenyl group are selected from the group consisting of halogen, lower-alkoxy, and combinations thereof;

$R_1$ is an alkyl group selected from the group consisting of lower-alkyl, lower-alkenyl, and lower-alkoxy lower-alkyl, having from 2 to 6 carbon atoms;

$R_2$ is a heterocyclic lower-alkyl ring system selected from the group consisting of pyrrolyl lower-alkyl, pyrazolyl lower-alkyl, imidazolyl lower-alkyl, imidazolinyl lower-alkyl, imidazolyl lower-thioalkyl, triazolyl lower-alkyl, triazolyl lower-thioalkyl, tetrazolyl lower-alkyl, tetrazolyl lower-thioalkyl, thienyl lower-oxyalkyl, thienyl lower-hydroxyalkyl, thien-3-yl lower-alkyl, furanyl lower-hydroxyalkyl, thiazolyl lower-alkyl, oxazolyl lower-alkyl, thiadiazolyl lower-alkyl, oxadiazolyl lower-alkyl, piperidinyl lower-alkyl, pyrimidinyl lower-alkyl, pyridazinyl lower-alkyl, triazinyl lower-alkyl, indolyl lower-alkyl, isoindolyl lower-alkyl, benzimidazolyl lower-alkyl, benzopyrazolyl lower-alkyl, benzoxazolyl lower-alkyl, benzopyranyl lower-alkyl, benzodioxanyl lower-alkyl, benzothiazinyl lower-alkyl, quinazolinyl lower-alkyl, purinyl lower-alkyl, phthalimidyl lower-alkyl, naphthalenecarboxamidyl lower-alkyl, and naphthalenesulfamidyl lower-alkyl, wherein the heterocyclic ring system may be unsubstituted or substituted;

$R_3$ is selected from the group consisting of hydrogen, lower-alkoxy carbonyl and lower-alkoxy methyl; and $R_4$ is selected from the group consisting of hydrogen and methyl.

DETAILED DESCRIPTION OF THE INVENTION

The compounds of the pretest invention possess very desirable analgesic activities. In particular, the inventive compounds have central nervous system depressant properties which include analgesia, hypnosis, sedation, muscle relaxation, increased pain threshold, and barbiturate and/or generally anesthetic potentiation. Many of the compound provide highly potent analgesia with immediate onset and a short duration of action. These properties are highly desirable in circumstances where acute sever pain must be eliminated over a short period of time, such as in anesthesiology. The preferred compounds of the present invention have been found to provide reduced rigidity at high doses, superior motor coordination recovery, or less respiratory depressive and/or cardiovascular depressive activity when compared to fentanyl (N-phenyl-N-[1-(2-phenylethyl)-4-piperidinyl]propanamide).

The compounds of the present invention may be used together with a pharmaceutically acceptable carrier to provide pharmaceutical compositions and can be administered to mammals such as man in amounts sufficient to provide analgesic effects.

As set out above, the analgesic compounds of the present invention have the general formula:

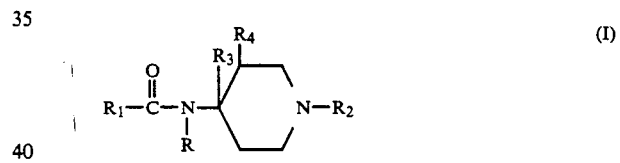

including optically active isomeric forms, and the pharmaceutically acceptable acid addition salts thereof, wherein R, $R_1$, $R_2$, $R_3$ and $R_4$ are defined as set forth below:

R in Formula I above is an aryl group selected from the group consisting of Phenyl and substituted phenyl, wherein said substituents are selected from the group consisting of halogen, lower-alkoxy, and combinations thereof. Preferred substituents are fluoro and methoxy. The preferred position for attachment of a substituent to the phenyl ring is at the 2 (ortho) position. In a preferred embodiment, R is selected from the group consisting of phenyl, 2-fluorophenyl and 2-methoxyphenyl.

$R_1$ in Formula I above is selected from the group consisting of lower-alkyl, lower-alkenyl, and lower-alkoxy lower-alkyl having from 2 to 6 carbon atoms. In a preferred embodiment, $R_1$ is selected from the group consisting of ethyl, ethenyl, methoxymethyl and 1-methoxyethyl.

$R_2$ in Formula I above is a heterocyclic lower-alkyl ring system selected from the group consisting of monocyclic heterocyclic lower-alkyl ring systems having 5 to 6 ring member atoms and fused bicyclic and tricyclic heterocyclic lower-alkyl ring systems having 5 to 6 ring member atoms in each ring of the polycyclic ring system. The heteroatom is a member selected from the group consisting of nitrogen, sulfur and oxygen.

In a preferred embodiment, the heterocyclic lower-alkyl ring system is selected from the group consisting of pyrrolyl lower-alkyl, pyrazolyl lower-alkyl, imidazolyl lower-alkyl, imidazolinyl lower-alkyl, imidazolyl lower-thioalkyl, triazolyl lower-alkyl, triazolyl lower-thioalkyl, tetrazolyl lower-alkyl, tetrazolyl lower-thioalkyl, thienyl lower-oxyalkyl, thienyl lower-hydroxyalkyl, thien-3-yl lower-alkyl, furanyl lower-hydroxyalkyl, thiazolyl lower-alkyl, oxazolyl lower-alkyl, thiadiazolyl lower-alkyl, oxadiazolyl lower-alkyl, piperidinyl lower-alkyl, pyrimidinyl lower-alkyl, pyridazinyl lower-alkyl, triazinyl lower-alkyl, indolyl lower-alkyl, isoindolyl lower-alkyl, benzimidazolyl lower-alkyl, benzopyrazolyl lower-alkyl, benzoxazolyl lower-alkyl, benzopyranyl lower-alkyl, benzodioxanyl lower-alkyl, benzothiazinyl lower-alkyl, quinazolinyl lower-alkyl, purinyl lower-alkyl, phthalimidyl lower-alkyl, naphthalenecarboxamidyl lower-alkyl, and naphthalenesulfamidyl lower-alkyl.

In a more preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, imidazolin-1-yl lower-alkyl, triazol-1-yl lower-alkyl, triazol-3-yl lower-thioalkyl, tetrazol-1-yl lower-alkyl, tetrazol-2-yl lower-alkyl, tetrazol-5-yl lower-thioalkyl, thien-2-yl lower-oxyalkyl, thien-2-yl lower-hydroxyalkyl, thien-3-yl lower-alkyl, furan-2-yl lower-hydroxyalkyl, thiazol-5-yl lower-alkyl, oxazol-3-yl lower-alkyl, thiadiazol-2-yl lower-alkyl, oxadiazol-3-yl lower-alkyl, piperidin-1-yl lower-alkyl, pyrimidin-1-yl lower-alkyl, pyridazin-1-yl lower-alkyl, triazin-1-yl lower-alkyl, indol-1-yl lower-alkyl, isoindol-2-yl lower-alkyl, benzimidazol-1-yl lower-alkyl, benzimidazol-2-yl lower-alkyl, benzopyrazol-3-yl lower-alkyl, benzoxazol-3-yl lower-alkyl, benzopyran-4-yl lower-alkyl, benzopyran-7-Yl lower-alkyl, benzodioxan-2-yl lower-alkyl, benzodioxan-8-yl lower-alkyl, benzothiazin-4-yl lower-alkyl, quinazolin-3-yl lower-alkyl, purin-1-yl lower-alkyl, purin-7-yl lower-alkyl, N-phthalimidyl lower-alkyl, N-naphthalenecarboxamidyl lower-alkyl, and N-naphthalenesulfamidyl lower-alkyl.

In a most preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, imidazolin-1-yl lower-alkyl, triazol-1-yl lower-alkyl, triazol-3-yl lower-thioalkyl, tetrazol-1-yl lower-alkyl, tetrazol-2-yl lower-alkyl, tetrazol-5-yl lower-thioalkyl, furan-2-1 lower-hydroxyalkyl, oxazol-3-yl lower-alkyl, thiadiazol-2-yl lower-alkyl, oxadiazol-3-yl lower-alkyl, piperidin-1-yl lower-alkyl, pyrimidin-1-yl lower-alkyl, pyridazin-1-yl lower-alkyl, triazin-1-yl lower-alkyl, indol-1-yl lower-alkyl, isoindol-2-yl lower-alkyl, benzimidazol-1-yl lower-alkyl, benzimidazol-2-yl lower-alkyl, benzopyrazol-3-yl lower-alkyl, benzoxazol-3-yl lower-alkyl, benzopyran-4-yl lower-alkyl, benzopyran-7-yl lower-alkyl, benzodioxan-2-yl lower-alkyl, benzodioxan-8-yl lower-alkyl, benzothiazin-4-yl lower-alkyl, quinazolin-3-yl lower-alkyl, purin-1-yl lower-alkyl, purin-7-yl lower-alkyl, N-phthalimidyl lower-alkyl, N-naphthalenecarboxamidyl lower-alkyl, and N-naphthalenesulfamidyl lower-alkyl.

The heterocyclic ring may be unsubstituted or substituted, wherein the substituent group is independently selected from the group consisting of halogen, oxygen, hydroxyl, nitro, amino, carbonyl, lower-alkoxy carbonyl, lower-alkyl, lower-cycloalkyl, lower-alkoxy, lower-thioalkyl, halogenated lower-alkyl, aryl, halogenated aryl, heterocycles, and combinations thereof. In a preferred embodiment, the substituent group is selected from the group consisting of fluoro, chloro, iodo, oxygen, nitro, amino, carbonyl, ethoxy carbonyl, methyl, ethyl, isopropyl, spiroethane, methoxy, thiomethyl, trifluoromethyl, phenyl, morpholinyl and combinations thereof.

The lower-alkyl group is selected from the group consisting of branched- or unbranched-hydrocarbon groups containing from 1 to 7 carbon atoms. The lower-alkyl group may be substituted or unsubstituted, with substituent members independently selected from the group consisting of oxygen, hydroxyl, sulfur, and combinations thereof. In a preferred embodiment, the lower-alkyl group is selected from the group consisting of methyl, ethyl, 2-hydroxyethyl, 2-oxoethyl, and 2-thioethyl.

$R_3$ in Formula I above is selected from the group consisting of hydrogen, lower-alkoxy carbonyl and lower-alkoxy methyl. In a preferred embodiment, the $R_3$ group is selected from the group consisting of hydrogen, methoxy carbonyl and methoxymethyl.

$R_4$ in Formula I above is selected hydrogen and methyl.

In a preferred embodiment, the compounds of the present invention have the general formula:

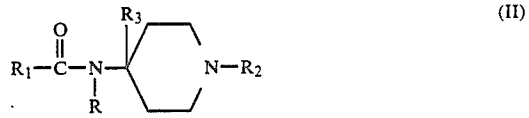

(II)

including optically active isomeric forms, and the pharmaceutically acceptable acid addition salts thereof, wherein R and $R_1$ are as defined above and $R_2$ is a heterocyclic lower-alkyl ring system selected from the group consisting of pyrrolyl lower-alkyl, pyrazolyl lower-alkyl, imidazolyl lower-alkyl, imidazolyl lower-thioalkyl, triazolyl lower-alkyl, triazolyl lower-thioalkyl, tetrazolyl lower-alkyl, tetrazolyl lower-thioalkyl, thienyl lower-oxyalkyl, thienyl lower-hydroxyalkyl, thien-3-yl lower-alkyl, furanyl lower-hydroxyalkyl, thiazolyl lower-alkyl, oxazolyl lower-alkyl, thiadiazolyl lower-alkyl, oxadiazolyl lower-alkyl, piperidinyl lower-alkyl, pyrimidinyl lower-alkyl, pyridazinyl lower-alkyl, triazinyl lower-alkyl, indolyl lower-alkyl, isoindolyl lower-alkyl, benzimidazolyl lower-alkyl, benzopyrazolyl lower-alkyl, benzoxazolyl lower-alkyl, benzopyranyl lower-alkyl, benzodioxanyl lower-alkyl, benzothiazinyl lower-alkyl, quinazolinyl lower-alkyl, purinyl lower-alkyl, naphthalenecarboxamidyl lower-alkyl, and naphthalenesulfamidyl lower-alkyl.

In a preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, triazol-1-yl lower-alkyl, triazol-3-yl lower-thioalkyl, tetrazol-2-yl lower-alkyl, tetrazol-5-yl lower-thioalkyl, thien-2-yl lower-oxyalkyl, thien-2-yl lower-hydroxyalkyl, thien-3-yl lower-alkyl, furan-2-yl lower-hydroxyalkyl, thiazol-5-yl lower-alkyl, oxazol-3-yl lower-alkyl, thiadiazol-2-yl lower-alkyl, oxadiazol-3-yl lower-alkyl, piperidin-1-yl lower-alkyl, pyrimidin-1-yl lower-alkyl, pyridazin-1-yl lower-alkyl, triazin-1-yl lower-alkyl, indol-1-yl lower-alkyl, isoindol-2-yl lower-alkyl, benzimidazol-1-yl lower-alkyl, benzimidazol-2-yl lower-alkyl, benzopyrazol-3-yl lower-alkyl, benzoxazol-3-yl lower-alkyl, benzopyran-4-yl lower-alkyl, benzopyran-7-yl lower-alkyl, benzodioxan-2-yl lower-alkyl, benzodioxan-8-yl lower-alkyl, benzothiazin-4-yl lower-alkyl, quinazolin-3-yl lower-alkyl, purin-1-yl lower-alkyl, purin-7-yl lower-alkyl, N-naphthalenecarboxamidyl lower-alkyl, and N-naphthalenesulfamidyl lower-alkyl.

In a more preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, triazol-1-yl lower-alkyl, triazol-3-yl lower-thioalkyl, tetrazol-2-yl lower-alkyl, tetrazol-5-yl lower-thioalkyl, furan-2-yl lower-hydroxyalkyl, oxazol-3-yl lower-alkyl, thiadiazol-2-yl lower-alkyl, oxadiazol-3-yl lower-alkyl, piperidin-1-yl lower-alkyl, pyrimidin-1-yl lower-alkyl, pyridazin-1-yl lower-alkyl, triazin-1-yl lower-alkyl, indol-1-yl lower-alkyl, isoindol-2-yl lower-alkyl, benzimidazol-1-yl lower-alkyl, benzimidazol-2-yl lower-alkyl, benzopyrazol-3-yl lower-alkyl, benzoxazol-3-yl lower-alkyl, benzopyran-4-yl lower-alkyl, benzopyran-7-yl lower-alkyl, benzodioxan-2-yl lower-alkyl, benzodioxan 8-yl lower-alkyl, benzothiazin-4-yl lower-alkyl, quinazolin-3-yl lower-alkyl, purin-1-yl lower-alkyl, purin-7-yl lower-alkyl, N-naphthalenecarboxamidyl lower-alkyl, and N-naphthalenesulfamidyl lower-alkyl.

The heterocyclic ring may be unsubstituted or substituted, wherein the substituent group is selected from the group consisting of halogen, oxygen, hydroxyl, nitro, amino, carbonyl, lower-alkoxy carbonyl, lower-alkyl, lower-cycloalkyl, lower-alkoxy, lower/thioalkyl, halogenated lower-alkyl, aryl, halogenated aryl, heterocyclics, and combinations thereof. In a preferred embodiment, the substituent group is selected from the group consisting of fluoro, chloro, iodo, oxygen, nitro, amino, carbonyl, ethoxy carbonyl, methyl, ethyl, isopropyl, spiroethane, methoxy, thiomethyl, trifluoromethyl, phenyl, morpholinyl and combinations thereof.

The lower-alkyl group is selected from the group consisting of branched or unbranched-hydrocarbon groups containing from 1 to 7 carbon atoms. The lower-alkyl group may be substituted or unsubstituted, with substituent members independently selected from the group consisting of oxygen, hydroxyl, sulfur, and combinations thereof. In a preferred embodiment, the lower-alkyl group is a member selected from the group consisting of methyl, ethyl, 2-hydroxyethyl, 2-oxoethyl, and 2-thioethyl.

$R_3$ is selected from the group consisting of lower-alkoxy carbonyl and lower-alkoxy methyl. In a preferred embodiment, the $R_3$ group is selected from the group consisting of methoxy carbonyl and methoxymethyl.

In another preferred embodiment, the compounds of the present invention have the general formula:

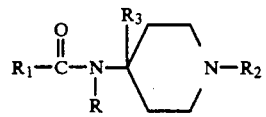
(II)

including optically active isomeric forms, and the pharmaceutically acceptable acid addition salts thereof, wherein R, and $R_1$ are as defined above, $R_2$ is a heterocyclic lower-alkyl ring system selected from the group consisting of pyrrolyl lower-alkyl, pyrazolyl lower-alkyl, imidazolyl lower-alkyl, imidazolyl lower-thioalkyl, triazolyl lower-alkyl, triazolyl lower-thioalkyl, tetrazolyl lower-alkyl, tetrazolyl lower-thioalkyl, thienyl lower-oxyalkyl, thienyl lower-hydroxyalkyl, thien-3-yl lower-alkyl, thiazolyl lower-alkyl, oxazolyl lower-alkyl, thiadiazolyl lower-alkyl, oxadiazolyl lower-alkyl, piperidinyl lower-alkyl, pyrimidinyl lower-alkyl, pyridazinyl lower-alkyl, triazinyl lower-alkyl, indolyl lower-alkyl, isoindolyl lower-alkyl, benzimidazolyl lower-alkyl, benzopyrazolyl lower-alkyl, benzoxazolyl lower-alkyl, benzopyranyl lower-alkyl, benzodioxanyl lower-alkyl, benzothiazinyl lower-alkyl, quinazolinyl lower-alkyl, purinyl lower-alkyl, naphthalenecarboxamidyl lower-alkyl, and naphthalenesulfamidyl lower-alkyl.

In more preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, triazol-1-yl lower-alkyl, tetrazol-2-yl lower-alkyl, tetrazol-5-yl lower-thioalkyl, 2-thienyl lower-oxyalkyl, 2-thienyl lower-hydroxyalkyl, thien-3-yl lower-alkyl, thiazol-5-yl lower-alkyl, oxazol-3-yl lower-alkyl, thiadiazol-2-yl lower-alkyl, oxadiazol-3-yl lower-alkyl, piperidin-1-yl lower-alkyl, pyrimidin-1-yl lower-alkyl, pyridazin-1-yl lower-alkyl, triazin-1-yl lower-alkyl, indol-1-yl lower- alkyl, isoindol-2-yl lower-alkyl, benzimidazol-1-yl lower-alkyl, benzimidazol-2-yl lower-alkyl, benzopyra- zol-3-yl lower-alkyl, benzoxazol-3-yl lower-alkyl, benzopyran-4-yl lower-alkyl, benzodioxan-2-yl lower-alkyl, benzothiazin-4-yl lower-alkyl, quinazolin-3-yl lower- alkyl, purin-1-yl lower-alkyl, purin-7-yl lower-alkyl, N-naphthalenecarboxamidyl lower-alkyl, and N-naphthalenesulfamidyl lower-alkyl.

In a most preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, triazol-1-yl lower-alkyl, tetrazol-2-yl lower-alkyl, tetrazol-5-yl lower-thioalkyl, oxazol-3-yl lower-alkyl, thiadiazol-2-yl lower-alkyl, oxadiazol-3-yl lower-alkyl, piperidin-1-yl lower-alkyl, pyrimidin-1-yl lower-alkyl, pyridazin-1-yl lower-alkyl, triazin-1-yl lower-alkyl, indol-1-yl lower-alkyl, isoindol-2-yl lower-alkyl, benzimidazol-1-yl lower-alkyl, benzimidazol-2-yl lower-alkyl, benzopyrazol-3-yl lower-alkyl, benzoxazol-3-yl lower-alkyl, benzopyran-4-yl lower-alkyl, benzodioxan-2-yl lower-alkyl, benzothiazin-4-yl lower-alkyl, quinazolin-3-yl lower-alkyl, purin-1-yl lower-alkyl, purin-7-yl lower-alkyl, N-naphthalenecarboxamidyl lower-alkyl, and N-naphthalenesulfamidyl lower-alkyl.

$R_3$ is a lower-alkoxy carbonyl group, preferably methoxy carbonyl.

The heterocyclic ring may be unsubstituted or substituted, wherein the substituent group is selected from the group consisting of halogen, oxygen, hydroxyl, nitro, amino, carbonyl, lower-alkoxy carbonyl, lower-alkyl, lower-cycloalkyl, lower-alkoxy, lower-thioalkyl, halogenated lower-alkyl, aryl, halogenated aryl, heterocyclics, and combinations thereof. In a preferred embodiment, the substituent group is a member selected from the group consisting of fluoro, chloro, iodo, oxygen, nitro, amino, carbonyl, ethoxy carbonyl, methyl, ethyl, isopropyl, spiroethane, methoxy, thiomethyl, trifluoromethyl, phenyl, morpholinyl and combinations thereof.

The lower-alkyl group is selected from the group consisting of branched- or unbranched-hydrocarbon groups containing from 1 to 7 carbon atoms. The lower-alkyl group may be substituted or unsubstituted, with substituent members selected from the group consisting of oxygen, hydroxyl, sulfur, and combinations thereof. In a preferred embodiment, the lower-alkyl group is selected from the group consisting of methyl, ethyl, 2-hydroxyethyl, 2-oxoethyl, and 2-thioethyl.

In another preferred embodiment, the compounds of the present invention have the general formula:

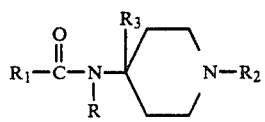

(II)

including optically active isomeric forms, and the pharmaceutically acceptable acid addition salts thereof, wherein R and $R_1$ are as defined above, $R_2$ is a heterocyclic lower-alkyl ring system selected from the group consisting of pyrrolyl lower-alkyl, pyrazolyl lower-alkyl, imidazolyl lower-alkyl, imidazolyl lower-thioalkyl, triazolyl lower-alkyl, triazolyl lower-thioalkyl, tetrazolyl lower-alkyl, tetrazolyl lower-thioalkyl, thienyl lower-oxyalkyl, thienyl lower-hydroxyalkyl, thien-3-yl lower-alkyl, furanyl lower-hydroxyalkyl, thiazolyl lower-alkyl, pyrimidinyl lower-alkyl, indolyl lower-alkyl, isoindolyl lower-alkyl, benzimidazolyl lower-alkyl, benzopyranyl lower-alkyl, benzodioxanyl lower-alkyl, quinazolinyl lower-alkyl, purinyl lower-alkyl, and naphthalenecarboxamidyl lower-alkyl.

In a preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, triazol-1-yl lower-alkyl, triazol-3-yl lower-thioalkyl, tetrazol-2-yl lower-alkyl, tetrazol-5-yl lower-thioalkyl, thien-2-yl lower-oxyalkyl, thien-2-yl lower-hydroxyalkyl, thien-3-yl lower-alkyl, furan-2-yl lower-hydroxyalkyl, thiazol-5-yl lower-alkyl, pyrimidin-1-yl lower-alkyl, indol-1-yl lower-alkyl, isoindol-2-yl lower-alkyl, benzimidazol-1-yl lower-alkyl, benzoxazol-3-yl lower-alkyl, benzopyran-4-yl lower-alkyl, benzopyran-7-yl lower-alkyl, benzodioxan-2-yl lower-alkyl, benzodioxan-8-yl lower-alkyl, quinazolin-3-yl lower-alkyl, purin-1-yl lower-alkyl, purin-7-yl lower-alkyl, and N-naphthalenecarboxamidyl lower-alkyl.

In a more preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, triazol-1-yl lower-alkyl, triazol-3-yl lower-thioalkyl, tetrazol-2-yl lower-alkyl, tetrazol-5-yl lower-thioalkyl, furan-2-yl lower-hydroxyalkyl, pyrimidin-1-yl lower-alkyl, indol-1-yl lower-alkyl, isoindol-2-yl lower-alkyl, benzimidazol-1-yl lower-alkyl, benzoxazol-3-yl lower-alkyl, benzopyran-4-yl lower-alkyl, benzopyran-7-yl lower-alkyl, benzodioxan-2-yl lower-alkyl, benzodioxan-8-yl lower-alkyl, quinazolin-3-yl lower-alkyl, purin-1-yl lower-alkyl, purin-7-yl lower-alkyl, and N-naphthalenecarboxamidyl lower-alkyl.

The heterocyclic ring may be unsubstituted or substituted, wherein the substituent group is a member independently selected from the group consisting of halogen, oxygen, hydroxyl, nitro, amino, carbonyl, lower-alkoxy carbonyl, lower-alkyl, lower-cycloalkyl, lower-alkoxy, lower-thioalkyl, halogenated lower-alkyl, aryl, halogenated aryl, heterocyclics, and combinations thereof. In a preferred embodiment, the substituent group is a member selected from the group consisting of fluoro, chloro, iodo, oxygen, nitro, amino, carbonyl, ethoxy carbonyl, methyl, ethyl, isopropyl, spiroethane, methoxy, thiomethyl, trifluoromethyl, phenyl, morpholinyl and combinations thereof.

The lower-alkyl group is a member selected from the group consisting of branched or unbranched hydrocarbon groups containing from 1 to 7 carbon atoms. The lower-alkyl group may be substituted or unsubstituted, with substituent members independently selected from the group consisting of oxygen, hydroxyl, sulfur, and combinations thereof. In a preferred embodiment, the lower-alkyl group is a member selected from the group consisting of methyl, ethyl, 2-hydroxyethyl, 2-oxoethyl, and 2-thioethyl.

$R_3$ is a lower-alkoxy methyl group. In a preferred embodiment, the $R_3$ group is methoxymethyl.

In another preferred embodiment, the compounds of the present invention have the general formula:

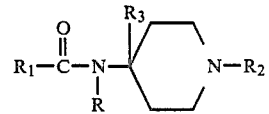

(II)

including optically active isomeric forms, and the pharmaceutically acceptable acid addition salts thereof wherein:

R is a n aryl group selected from the group consisting of phenyl and substituted phenyl, wherein said substituents are selected from the group consisting of halogen, lower-alkoxy, and combinations thereof. Preferred substituents are fluoro or methoxy. The preferred position for attachment of a substituent to the phenyl ring is at the 2 (ortho) position. In a preferred embodiment, R is selected from the group consisting of phenyl, 2-fluorophenyl and 2-methoxyphenyl. In a more preferred embodiment, R is 2-fluorophenyl or 2-methoxyphenyl.

$R_1$ is selected from the group consisting of lower-alkyl, lower-alkenyl, lower-alkyl and lower-alkoxy having from 2 to 6 carbon atoms. In a preferred embodiment, $R_1$ is selected from the group consisting of ethyl, ethenyl, methoxymethyl and 1-methoxyethyl.

$R_2$ is a heterocyclic lower-alkyl ring system selected from the group consisting of pyrazolyl lower-alkyl, imidazolyl lower-alkyl, imidazolinyl lower-alkyl, benzimidazolyl lower-alkyl, and phthalimidyl lower-alkyl. In a preferred embodiment, the heterocyclic lower-alkyl ring system is selected from the group consisting of pyrazol-1-yl lower-alkyl, imidazol-1-yl lower-alkyl, imidazolin-1-yl lower-alkyl, benzimidazol-1-yl lower-alkyl, and N-phthalimidyl lower-alkyl.

The heterocyclic ring may be unsubstituted or substituted, wherein said substituents are selected from the group consisting of halogen, oxygen, hydroxyl, nitro, amino, carbonyl, lower-alkoxy carbonyl, lower-alkyl, lower-cycloalkyl, lower-alkoxy, lower/thioalkyl, halogenated lower-alkyl, aryl, halogenated aryl, heterocyclics, and combinations thereof. In a preferred embodiment, the substituents are selected from the group consisting of fluoro, chloro, iodo, oxygen, nitro, amino, carbonyl, ethoxy carbonyl, methyl, ethyl, isopropyl, spiroethane, methoxy, thiomethyl, trifluoromethyl, phenyl, halogenated aryl, morpholinyl and combinations thereof. In a more preferred embodiment, the substituents are selected from the group consisting of methyl, ethyl, nitro, halogenated aryl and combinations thereof.

The lower-alkyl group is branched- or unbranched-hydrocarbon group containing from 1 to 7 carbon atoms. The lower-alkyl group may be substituted or unsubstituted, with substituents being selected from the group consisting of oxygen, hydroxyl, sulfur, and combinations thereof. In a preferred embodiment, the lower-alkyl group is selected from the group consisting of methyl, ethyl, 2-hydroxyethyl, 2-oxoethyl, and 2-thioethyl, most preferably an ethyl group.

$R_3$ is selected from the group consisting of lower-alkoxy carbonyl and lower-alkoxy methyl. In a preferred embodiment, the $R_3$ group is a member selected from the group consisting of methoxy carbonyl and methoxymethyl.

In another preferred embodiment, the compounds of the present invention have the general formula:

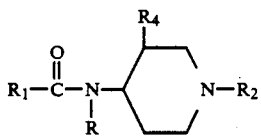

(III)

including optically active isomeric forms, and the pharmaceutically acceptable acid addition salts thereof, wherein:

R is an aryl group selected from the group consisting of phenyl substituted phenyl, wherein said substituents are selected from the group consisting of halogen, lower-alkoxy, and combinations thereof. Preferred substituents are fluoro and methoxy. The preferred position for attachment of a substituent to the phenyl ring is at the 2 (ortho) position. In a preferred embodiment, R is selected from the group consisting of phenyl, 2-fluorophenyl and 2-methoxyphenyl, most preferably, 2-fluorophenyl.

$R_1$ is selected from the group consisting of lower-alkyl, lower-alkenyl, and lower-alkoxy lower-alkyl having from 2 to 6 carbon atoms. In a preferred embodiment, $R_1$ is selected from the group consisting of ethyl, ethenyl, methoxymethyl and 1-methoxyethyl. In a more preferred embodiment, $R_1$ is ethyl and methoxymethyl.

$R_2$ is a heterocyclic lower-alkyl ring system selected from the group consisting of pyrrolyl lower-alkyl, pyrazolyl lower-alkyl, imidazolyl lower-alkyl, imidazolyl lower-thioalkyl, triazolyl lower-alkyl, triazolyl lower-thioalkyl, tetrazolyl lower-alkyl, tetrazolyl lower thioalkyl, thienyl lower-oxyalkyl, thienyl lower-hydroxyalkyl, thien-3-yl lower-alkyl, furanyl lower-hydroxyalkyl, thiazolyl lower-alkyl, oxazolyl lower-alkyl, thiadiazolyl lower-alkyl, oxadiazolyl lower-alkyl, piperidinyl lower-alkyl, pyrimidinyl lower-alkyl, pyridazinyl lower-alkyl, triazinyl lower-alkyl, indolyl lower alkyl, isoindolyl lower-alkyl, benzimidazolyl lower-alkyl, benzopyrazolyl lower-alkyl, benzoxazolyl lower-alkyl, benzopyranyl lower-alkyl, benzodioxanyl lower-alkyl, benzothiazinyl lower-alkyl, quinazolinyl lower-alkyl, purinyl lower- alkyl, naphthalenecarboxamidyl lower-alkyl, and naphthalenesulfamidyl lower-alkyl.

In a preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, triazol-1-yl lower-alkyl, triazol-3-yl lower-thioalkyl, tetrazol-2-yl lower-alkyl, tetrazol-5-yl lower-thioalkyl, thien-2-yl lower-oxyalkyl, thien-2-yl lower-hydroxyalkyl, thien-3-yl lower-alkyl, furan-2-yl lower-hydroxyalkyl, thiazol-5-yl lower-alkyl, oxazol-3-yl lower-alkyl, thiadiazol-2-yl lower-alkyl, oxadiazol-3-yl lower-alkyl, piperidin-1-yl lower-alkyl, pyrimidin-1-yl lower-alkyl, pyridazin-1-yl lower-alkyl, triazin-1-yl lower-alkyl, indol-1-yl lower-alkyl, isoindol-2-yl lower-alkyl, benzimidazol-1-yl lower-alkyl, benzimidazol-2-yl lower-alkyl, benzopyrazol-3-yl lower-alkyl, benzoxazol-3-yl lower-alkyl, benzopyran-4-yl lower-alkyl, benzopyran-7-yl lower-alkyl, benzodioxan-2-yl lower-alkyl, benzodioxan-8-yl lower-alkyl, benzothiazin-4-yl lower-alkyl, quinazolin-3-yl lower-alkyl, purin-1-yl lower-alkyl, purin-7-yl lower-alkyl, N-naphthalenecarboxamidyl lower-alkyl, and N-naphthalenesulfamidyl lower-alkyl.

In a more preferred embodiment, the heterocyclic lower-alkyl ring system is selected from the group consisting of pyrrol-1-yl lower-alkyl, pyrazol-1-yl lower-alkyl, imidazol-1-yl lower-alkyl, imidazol-3-yl lower-alkyl, imidazol-4-yl lower-alkyl, imidazol-2-yl lower-thioalkyl, triazol-1-yl lower-alkyl, triazol-3-yl lower-thioalkyl, tetrazol-2-yl lower-alkyl, tetrazol-5-yl lower-thioalkyl, thien-2-yl lower-oxyalkyl, thien-2-yl lower-hydroxyalkyl, thien-3-yl lower-alkyl, furan-2-yl lower-hydroxyalkyl, thiazol-5-yl lower-alkyl, oxazol-3-yl lower-alkyl, thiadiazol-2-yl lower-alkyl, oxadiazol-3-yl lower-alkyl, piperidin-1-yl lower-alkyl, pyrimidin-1-yl lower-alkyl, pyridazin-1-yl lower-alkyl, triazin-1-yl lower-alkyl, indol-1-yl lower-alkyl, isoindol-2-yl lower-alkyl, benzimidazol-1-yl lower-alkyl, benzimidazol-2-yl lower-alkyl, benzopyrazol-3-yl lower-alkyl, benzoxazol-3-yl lower-alkyl, benzopyran-4-yl lower-alkyl, benzopyran-7-yl lower-alkyl, benzodioxan-2-yl lower-alkyl, benzodioxan-8-yl lower-alkyl, benzothiazin-4-yl lower-alkyl, quinazolin-3-yl lower-alkyl, purin-1-yl lower-alkyl, purin-7-yl lower-alkyl, N-naphthalenecarboxamidyl lower-alkyl, and N-naphthalenesulfamidyl lower-alkyl.

In a most preferred embodiment, the $R_2$ group is a heterocyclic lower-alkyl ring system selected from the group consisting of pyrazolyl lower-alkyl, tetrazolyl lower-alkyl, isoindolyl lower-alkyl, and benzimidazolyl lower-alkyl.

In another preferred embodiment, the heterocyclic lower-alkyl ring system is selected from the group consisting of pyrazol-1-yl lower-alkyl, tetrazol-1-yl lower-alkyl, tetrazol-2-yl lower-alkyl, isoindol-2-yl lower-alkyl, benzimidazol-1-yl lower-alkyl, and benzimidazol-2-yl lower-alkyl.

The heterocyclic ring may be unsubstituted or substituted, wherein the substituents are selected from the group consisting of halogen, oxygen, hydroxyl, nitro, amino, carbonyl, lower-alkoxy carbonyl, lower-alkyl, lower-cycloalkyl, lower-alkoxy, lower-thioalkyl, halogenated lower-alkyl, aryl, halogenated aryl, heterocyclics, and combinations thereof. In a preferred embodiment, the substituent group is selected from the group consisting of fluoro, chloro, iodo, oxygen, nitro, amino, carbonyl, ethoxy carbonyl, methyl, ethyl, isopropyl, spiroethane, methoxy, thiomethyl, trifluoromethyl, phenyl, halogenated aryl, morpholinyl and combinations thereof. In a more preferred embodiment, the substituent group is selected from the group consisting of methyl, ethyl, nitro, halogenated aryl and combinations thereof.

The lower-alkyl group is a branched- or unbranched-hydrocarbon containing from 1 to 7 carbon atoms. The lower-alkyl group may be substituted or unsubstituted, with substituents being selected from the group consisting of oxygen, hydroxyl, sulfur, and combinations thereof. In a preferred embodiment, the lower-alkyl group is selected from the group consisting of methyl, ethyl, 2-hydroxyethyl, 2-oxoethyl, and 2-thioethyl. In a more preferred embodiment, the lower-alkyl group is methyl or ethyl.

R$_4$ is methyl.

The term "lower-alkyl", as used herein, means branched- or unbranched-hydrocarbon groups containing from 1 to 7 carbon atoms. The term "lower-alkoxy", as used herein, means branched- or unbranched-hydrocarboxy groups containing from 1 to 7 carbon atoms. The term "lower-cycloalkyl", as used herein, means cyclic alkyl groups containing from 3 to 6 carbon atoms. Preferred heterocyclic groups include from 6 to 12 carbon atoms and can include the substituents discussed above in connection with heterocyclic groups. The term "halogen", as used herein, refers to the chemically related elements fluorine, chlorine, bromine and iodine.

The compounds of the present invention which have at least one asymmetric carbon atom can exist in optically active isomeric forms. For example, in compounds in which R$_2$ is a 2-phenyl-1-propyl or 1-phenyl-2-propyl group, etc., the carbon adjacent to the piperidinyl nitrogen is an asymmetric carbon atom and such compounds can therefore exist in optical active isomeric (enantiomeric) forms. Such isomeric forms can be isolated from the racemic mixtures by techniques known to those skilled in the art.

The compounds of the present invention which have an alkyl group as the R$_4$ group exist in cis or trans form. Such compounds can be used as a mixture of such forms but many times one form is more active than the other or has other desirable characteristics. Thus, many times it is desirable to resolve the cis/trans mixture. This resolution can be accomplished by techniques conventional in the art for such purpose, e.g., chromatographic techniques such as column chromatography or high pressure liquid chromatography or simple recrystallization techniques.

The compounds of the present invention can be prepared by various methods. In general, the desired compounds having Formulae I, II or III above can be prepared by reacting a compound having the formula:

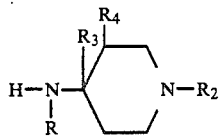

with a compound having the formula:

R$_1$—CO—X or (R$_1$CO)$_2$O or by reacting a compound having the formula:

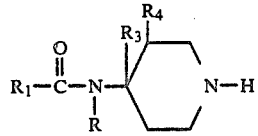

with a compound having the formula:

R$_2$X wherein the substituent groups R, R$_1$, R$_2$, R$_3$ and R$_4$ have the definitions set out above, and X represents halide or its reactive equivalent. Examples of halide reactive equivalents are toluene sulfonate, phenyl sulfonate, methyl sulfonate and the like.

In the first reaction, when the R$_2$ group is phenylmethyl (benzyl), the phenylmethyl group can be cleaved by hydrogenolysis or by reaction with 1-chloroethyl chloroformate followed by hydrolysis with methanol, see R. A. Olofson et al., *J. Org. Chem.*, 49, pp. 2081–2082 (1984), and replaced with other R$_2$ groups such as furanyl lower-alkyl, pyrazoyl lower-alkyl and the like. The preparation of secondary amines of the latter type has been described by P. G. H. Van Daele et al., *Arzneim-Forsch. Drug Res.*, 26, p. 1521, (1976).

Several convenient routes for the preparation of the compounds of the invention begin with known piperidone starting materials as shown below:

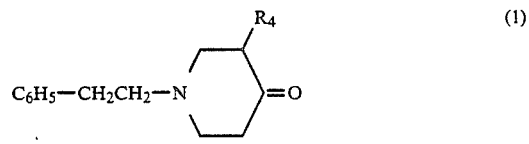
(1)

or

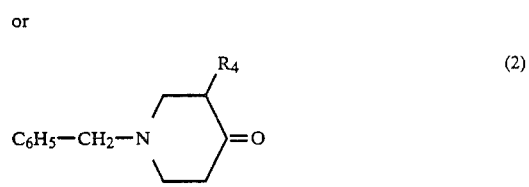
(2)

The compound 1-(2-phenylethyl)-4-piperidone (1), when R$_3$=H, or 1-(2-phenylethyl)-3-methyl-4-piperidone (1), when R$_3$=CH$_3$, can be prepared according to the procedure published by A. H. Becket, A. F. Casey and G. Kirk, *J. Med Pharm. Chem.*, Vol. 1, p. 37 (1959). The compound 1-phenylmethyl-4-piperidone (2), when R3=H, or 1-phenylmethyl-3-methyl-4-piperidone (2), when R$_3$=CH$_3$, can be prepared in an analogous manner by the procedure described by C. R. Ganellin and R. G. Spickch, *J. Med. Chem.*, Vol. 8, p. 619 (1965) or P. M. Carabateas and L. Grumbach, *J. Med. Pharm. Chem.*, Vol. 5, p. 913 (1962).

In one example of a method for preparing the compounds of the present invention, 1-phenylmethyl or 1 (2-phenylethyl)-4-piperidone is reacted with an unsubstituted or substituted heterocyclic amine to form a Schiff base. The Schiff base is then reduced, for example, with sodium borohydride to yield the unsubstituted or substituted 1-phenylmethyl or 1-(2-phenylethyl)-4-(N-heterocycloamine)-piperidine compound. See for example, S. Grossman et al., *Arch. Pharm.* (Weinheim)

311, p. 1010 (1978). The following reaction scheme, wherein R is a heterocyclic group within the definition of the present invention, illustrates such a method:

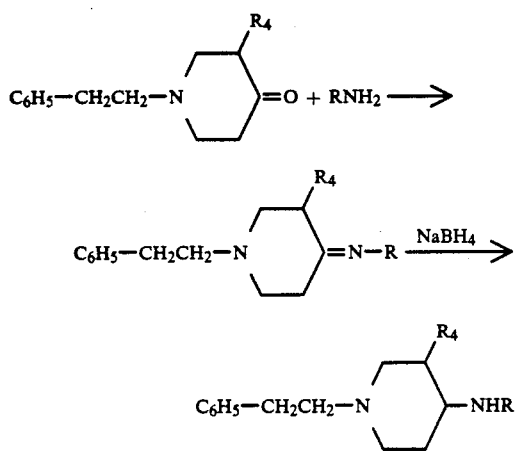

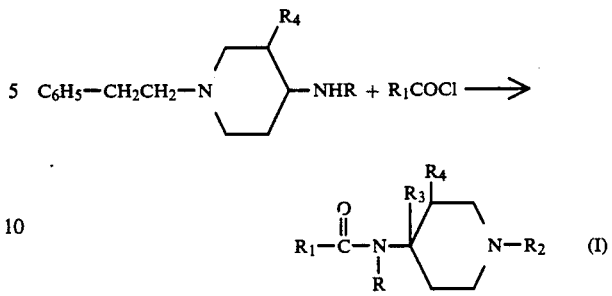

When the $R_4$ group is methyl, cis and trans isomers of compound (3) are created. The cis and trans isomers can be separated before or after reaction with an acid halide or anhydride, as set out above, thereby obtaining cis and trans isomers of compound (I) of the present invention. Separation of the cis/trans isomers can be carried out according to the following reaction scheme:

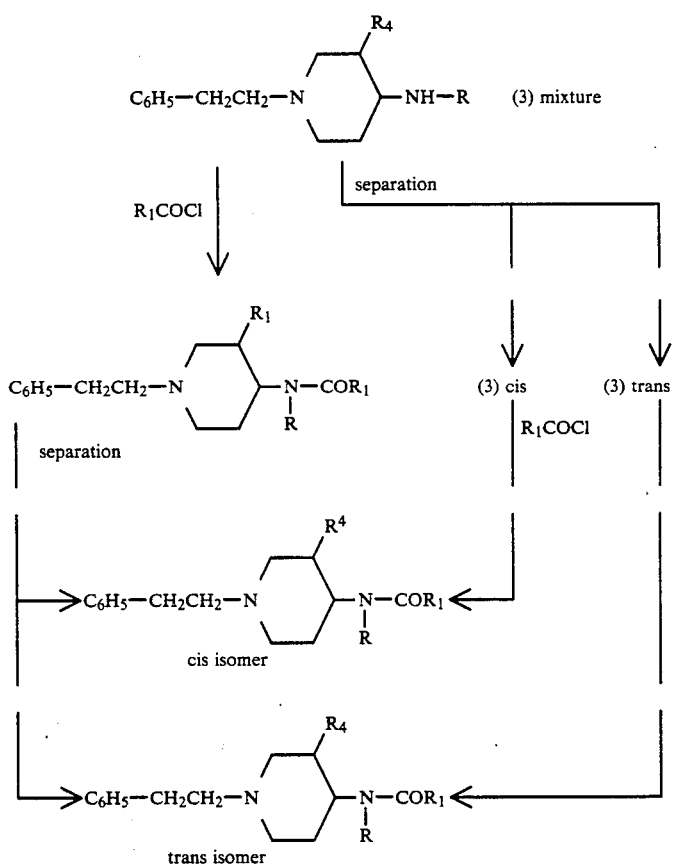

When the $R_4$ group is hydrogen, compound (3) can be reacted with an appropriate acid halide (e.g., $R_1COCl$) or an anhydride (e.g., $(R_1CO)_2O$) to introduce the desired $R_1$-carbonyl group on the nitrogen atom and thereby obtain compound (I) of the present invention, according to the reaction scheme shown below:

When the desired $R_2$ substituent group is not phenylethyl, one procedure for preparing compounds of the present invention with different $R_2$ groups is to remove the phenylmethyl group in compound (2) by hydrogenolysis (for example, using hydrogen over 10% palladium on carbon) or by reaction with 1-chloroethyl chloroformate above and replace it with a desired $R_2$ group. For example, compounds of the invention can be prepared according to the following scheme:

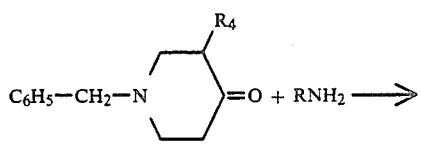

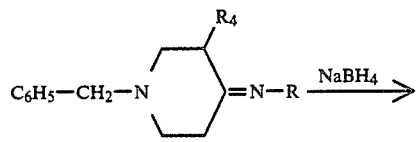

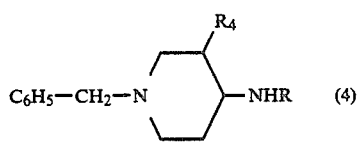

As set out above, when the R₄ group is methyl, compound (4) is a mixture of cis and trans isomers which can be separated prior to the next step. When the R₄ groups is hydrogen, no preliminary cis/trans isomer separation is necessary. After any such cis/trans separation, compound (4) can be reacted with hydrogen over palladium on carbon or with 1-chloroethyl chloroformate according to the following reaction scheme to remove the phenylmethyl group and prepare piperidinyl intermediate (5):

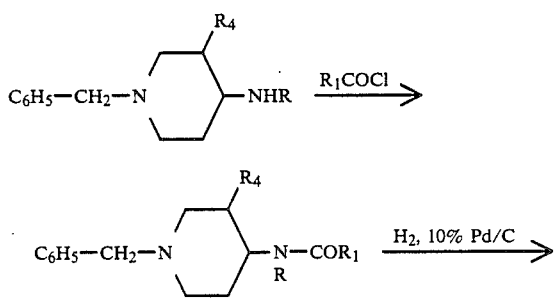

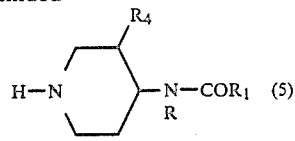

The desired $R_2$ substituent group can then be introduced by reacting compound (5) with an appropriately reactive molecule $R_2$-X, wherein X is halogen, such as chlorine, bromine, or iodine, or its reactive equivalent, to obtain compound (I) of the present invention according to the reaction scheme illustrated below:

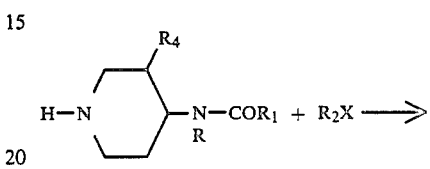

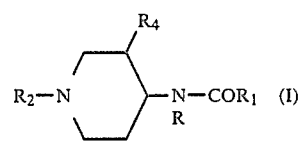

The reaction of $R_2$-X with a piperdinyl intermediate such as compound (5) can be conducted in an inert organic solvent such as, for example, an aromatic hydrocarbon, a ketone such as 4-methyl-2-pentanone and the like, an ether such as 1,4-dioxane, diethylether, tetrahydofuran, 1,2-dimethoxyethane and the like, or N,N-dimethylformamide or acetonitrile. The addition of an appropriate base, such as an alkali metal carbonate, may be utilized to neutralize the acid generated during the reaction. The addition of an iodide salt, such as an alkali metal iodide, may be appropriate. The temperature of the reaction mixture may be raised to increase the rate of reaction when appropriate.

In an alternative procedure, the phenylmethyl group can first be removed by hydrogenolysis or by reaction with 1-chloroethyl chloroformate prior to separation of the cis/trans isomers of compound (4) to obtain compound (I) of the present invention with the $R_1$ and $R_2$ groups introduced according to one of the two schemes shown below:

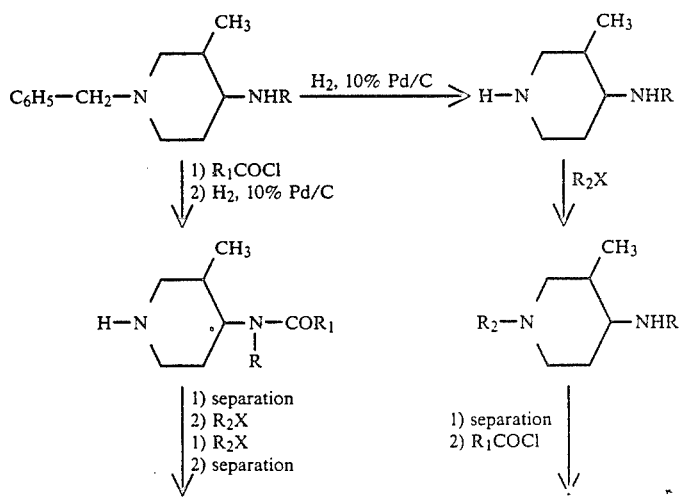

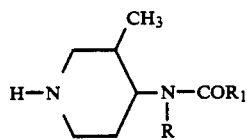

cis isomer

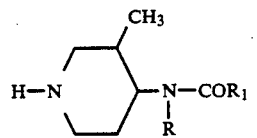

trans isomer

In a second example of a method for preparing the compounds of the present invention, an intermediate such as N-(phenylethyl)-4-piperidineamine (6) is utilized. In this method, the primary amine is reacted with a heterocycle group RX, where X is a halide or its reactive equivalent, to form a secondary amine precursor (7). The secondary amine is then acrylated. See, for example, Y. Zhu et al., *Acta Pharm. Sinica,* 16, p. 199 (1981). The following reaction scheme, wherein R is a heterocyclic group within the definition of the present invention, illustrates such a method to make compound (I) of the present invention.

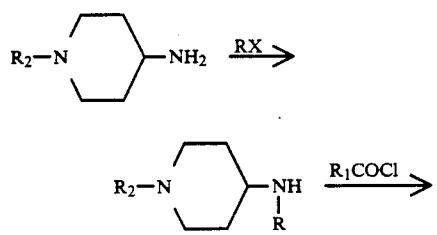

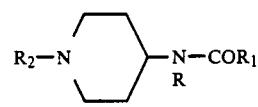

In a third example of a method for preparing the compounds of the present invention, the same intermediate, such as N-(phenylethyl)-4-piperidineamine (6), is utilized. In this method, the primary amine is reacted with an oxo-derivative of the heterocycle group R to form a secondary amine precursor. The oxo-intermediate is reduced prior to acylation. See, for example, Langhein et al., *Offenlegungschrift,* 234, p. 1965 (1975); *Chem. Abstr.* 82, 156121w (1975).

Compounds of the present invention which have 4,4-disubstitution can be prepared starting with, for example, N-phenylmethyl-4-piperidone by the following reaction scheme:

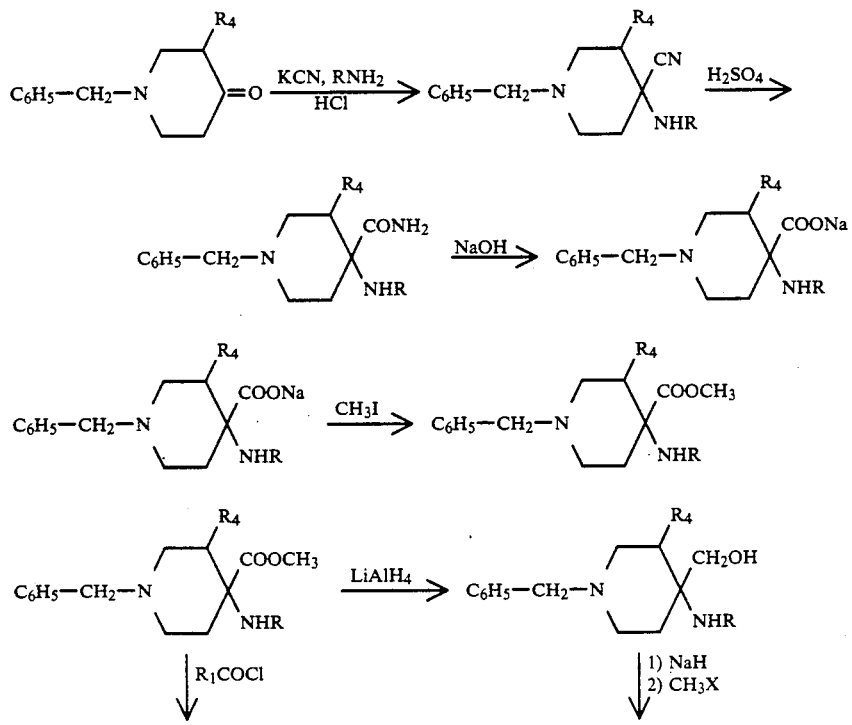

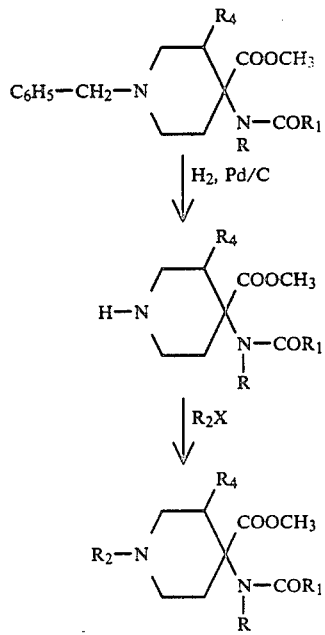

-continued

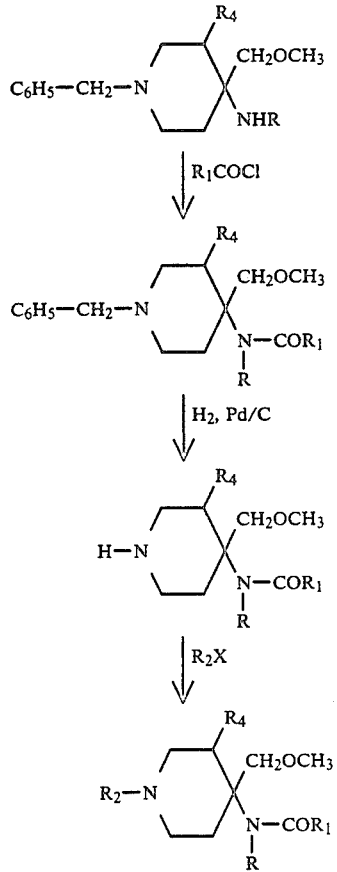

The compounds of the present invention while effective in the form of the free base may be formulated and administered in the form of the therapeutically or pharmaceutically acceptable acid addition salts for purposes of stability, convenience Of crystallization, increased solubility and the like. These acid addition salts include inorganic acid salts such as hydrochloric, hydrobromic, sulfuric, nitric, phosphoric, perchloric acid salts and the like; and organic acid salts such as acetic, trifluoroacetic, propionic, oxalic, hydroxyacetic, meth- oxyacetic, 2-hydroxypropanoic, 2/oxopropanoic, propanedioic, 2-hydroxy-butanedioic, benzoic, 2-hydroxybenzoic, 4-amino-2-hydroxy-benzoic, 3/phenyl-2-propenoic, alpha-hydroxybenzeneacetic, methanesulfonic, ethanesulfonic, benzenesulfonic, toluene-sulfonic, cyclohexanesulfamic, succinic, tartaric, citric, maleic, fumaric acid salts and the like. The preferred acid addition salts are chloride, oxalate and citrate. These acid addition salts can be prepared by conventional methods, such as by treatment of the free base of the inventive compound with the appropriate acid.

The compounds of the present invention, prepared in the free base form, can be combined with a pharmaceutically acceptable carrier to provide a pharmaceutical composition. Suitable carriers for the free bases include propylene glycol-alcohol-water, isotonic water, sterile water for injection (USP), emulphor TM -alcohol-water, cremophor-EL TM or other suitable carriers known to those skilled in the art.

The compounds of the present invention, prepared in the pharmaceutically acceptable acid addition salt form, can also be combined with a pharmaceutically acceptable carrier to provide a pharmaceutical composition. Suitable carriers for the acid addition salts include isotonic water, sterile water for injection (USP), alone or in combination with other solubilizing agents such as ethanol, propylene glycol, or other conventional solubilizing agents known to those skilled in the art.

Of course, the type of carrier will vary depending upon the mode of administration desired for the pharmaceutical composition as is conventional in the art. A preferred carrier is an isotonic aqueous solution of the inventive compound.

The compounds of the present invention can be administered to mammals, e.g., animals or humans, in amounts effective to provide the desired analgesic therapeutic effect or to reverse the actions of an opiate analgesic. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can be as low as about 0.00005 mg/kg, which the practitioner may titrate to the desired effect.

The compounds of the present invention can be administered parenterally, in the form of sterile solutions or suspensions, such as intravenously, intramuscularly or subcutaneously in the carriers previously described. The compounds may also be administered orally, in the form of pills, tablets, capsules, troches, and the like, as well as sublingually, rectally, or transcutaneously with a suitable pharmaceutically acceptable carrier for that particular mode of administration as is conventional in the art.

For parental therapeutic administration, the compounds of the present invention may be incorporated into a sterile solution or suspension. These preparations should contain at least about 0.1% of the inventive compound, by weight, but this amount may be varied to between about 0.1% and about 50% of the inventive compound, by weight of the parental composition. The exact amount of the inventive compound present in such compositions is such that a suitable dosage level will be obtained. Preferred compositions and preparations according to the present invention are prepared so that a paranteral dosage unit contains from between about 0.5 to about 100 milligrams of the inventive compound.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parental preparations may be enclosed in ampules, disposable syringes, or multiple dose vials made of glass or plastic.

The compounds of the present invention can also be administered orally. For oral therapeutic administration, the compounds may be incorporated with excipients and used in the form of tablets, capsules, elixirs, suspensions, syrups, wafers, chewing gums and the like. These preparations should contain at least about 4% of the inventive compound, by weight, but this amount may be varied depending upon the particular dosage form from between about 4% to about 70% of the inventive compound, by weight of the oral composition. The exact amount of the compound present in the composition is such that a suitable dosage will be obtained. Preferred compositions and preparations according to the present invention are prepared so that an oral dosage unit form contains from between about 5 to about 300 milligrams of the inventive compound.

The tablets, pills, capsules, troches and the like may also contain the following adjuvants: a binder, such as microcrystalline cellulose, gum tragacanth or gelatine; an excipient, such as starch or lactose; a disintegrating agent, such as alginic acid, Primogel, corn starch and the like; a lubricating agent, such as magnesium stearate or Sterotex; a gliding agent, such as colloidal silicon dioxide; a sweetening agent, such as sucrose or saccharin; and a flavoring agent, such as peppermint, methyl salicylate or orange flavoring. When the dosage form is a capsule, it may additionally contain a liquid carrier such as a fatty oil. Other dosage unit forms may contain other materials which modify the physical form of the dosage unit, such as enteric coatings. Thus tablets or pills may be coated with sugar, shellac, or other enteric coating agents. A syrup may contain, in addition to the above adjuvants, sucrose as a sweetening agent, preservatives, dyes, coloring agents and flavoring agents.

It is especially advantageous to formulate the pharmaceutical compositions in dosage unit forms for ease of administration and uniformity of dosage. The term dosage unit forms as used herein refers to physically discrete units suitable for use as a unitary dosage, each unit containing a predetermined quantity of active ingredient calculated to produce the desired therapeutic effect in association with the pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is further illustrated by the following examples which are presented for purposes of demonstrating, but not limiting, the preparation of the compounds and compositions of this invention.

EXAMPLE 1

This Example illustrates the preparation of secondary amine intermediate compounds.

The preparation of secondary amine intermediate compounds of type (9) having the general formula:

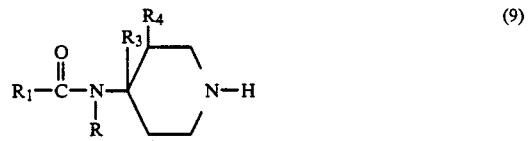

wherein the substituent groups R, $R_1$, $R_3$, and $R_4$ have the definitions set out above, has been described in, for example, U.S. Pat. No. 4,584,303, P. G. H. Van Daele et al., *Arzneim-Forsch. Drug Res.*, 26 p. 1521, (1976).

EXAMPLE 2

This Example illustrates the preparation of heterocyclic alkyl electrophile intermediate compounds.

The compounds of the present invention were prepared essentially by reacting secondary amine intermediate compounds of type (9) from Example 1 with an appropriate heterocyclic alkyl electrophile intermediate compound of type (10) having the formula:

wherein the substituent group $R_2$ has the definition set out above and X is a halide or its reactive equivalent.

The heterocyclic alkyl electrophile intermediates of type (10) which are commercially available include 3-(2-chloroethyl)-2-oxazolinone (Aldrich Chemical Company, Inc. Milwaukee, Wis., "Aldrich"), 4-vinylpyridine (Aldrich), 3-(dimethylaminomethyl)indole (Aldrich), N-(2-bromoethyl)phthalimide (Aldrich), 2-(chloromethyl)-benzimidazole (Aldrich), 4-(bromomethyl)-7-methoxycoumarin (Aldrich , 8-chloromethyl-2-fluorobenzo-1,3-dioxane (Maybridge Chemical Company Ltd., Trevillett, Tintagel, Cornwall TL34 OHW United Kingdom, "Maybridge"), 3-(2-bromoethyl)-1,2,3,4-tetrahydro-2,4-dioxoquinazoline (Maybridge), 7-(2-chloroethyl)theophylline (Aldrich), and N-(2-chloroethyl -1,8-naphthalimide (Aldrich).

EXAMPLE 3

This Example illustrates the preparation of heterocyclic alkyl electrophile intermediate compounds.

The heterocyclic alkyl electrophile intermediates of type (10) which are available from previously published procedures include 1-(2-chloroethyl)-1H-pyrrole (Machin et al., *J. Med. Chem.*, 1984, 27, p. 508), 1-(2-tosylethyl)-1H-pyrazole (Carpio et al., *Can. J. Chem.*, 1982, 60, p. 2295 , 1-(2-chloroethyl)-1H-imidazole hydrochloride (Thomas et al., B. Ger. Offen. DE 3,438,919, 1986), 5-nitro-1-(2-chloroethyl)-1H-imidazole (Caplav et al.,

*Acta. Pharm. Jugosl.*, 1975, 25, p. 71 , 2-methyl-5-nitro-1-(2-chloroethyl)-1H-imidazole (Alcalde et al., *J. Heterocyclic Chem.*, 1984, 21, p. 1647), 4-(2-chloroethyl)-1H-imidazole hydrochloride (Turner et al., *J. Amer. Chem. Soc.* 1949, 71, p. 3476, the alcohol precursor for 4-(2-chloroethyl) imidazole hydrochloride was conveniently provided by the procedure of Hirsch et al., *J. Appl. Chem.*, 1969, 19, p. 83), 1-methyl-2-(2-chloroethylthio)-1H-imidazole (Tweit, R. C. Ger. Offen. DE 2348525, 1978; *Chem. Abstr.*, 1974, 81, 63626b), 2-(bromoacetyl)-thiophene (Kipnis et al., *J. Amer. Chem. Soc.*, 1949, 71, p. 10), 2-(bromoacetyl)furan (Loiseau et al., *Eur. J. Chem.*, 1987, 22, p. 457), 5-methyl-2-chloroacetylfuran (Best et al., *Tetrahedron Lett.*, 1981, 22, p. 4877), 1-(2-bromoethyl)-3-methyl-4-amino-5- (1H)-triazolinone (Malbec et al., *J. Heterocyclic Chem.*, 1984, 21, p. 1769), 3-methyl-1-(2-bromoethyl)-1,6-dihydro-1H-pyridazin-6-one (Toshihiro et al., *J. Med. Chem.*, 1982, 25, p. 975), 1-(2-chloroethyl)-1H-benzimidazole (Pozharski et al., *Khim. Geterotsikl. Soedin*, 1969, p. 869; *Chem. Abstr.*, 1969, 72, 111370b), (1'-(2-bromoethyl)spiro-cyclopropane)-1,3'-[3H]-indole-2'-(1'H)-one (Robertson et al., *J. Med. Chem.*, 1987, 30, p. 824) 6-(2-bromoacetyl)-1,3-benzoxazolin-2-one (Vaccher-Ledein et al., *Bull. Soc. Pharm. Lille.* 1981, 37, p. 89), 7-(2-bromoethoxy)-coumarin (Abyshev et al., *Khim.-Farm. Zh.*, 1985, 19, p. 756; *Chem. Abstr.*, 1985, 103, 13435g), and 2-methyl-3-(2-chloro-ethyl)-3,4-dihydroquinazolin-4-one (Singh, P., *J. Indian Chem.*, 1978, 55, p. 801).

EXAMPLE 4

This Example illustrates the preparation of halogenated heterocyclic alkyl electrophile intermediate compounds in sodium ethoxide in ethanol.

The heterocyclic alkyl electrophile intermediates of type (10), when not commercially available, were generally synthesized by three routes of alkylation. These routes include substitution of an appropriate heterocyclic intermediate with 2-bromochloroethane or 1,2-dibromoethane in (1) sodium ethoxide-ethanol, (2) sodium hydride-dimethylformamide, or (3) quaternary ammonium phase transfer medium. A few procedures included alkylation of a peripheral thio group. The alcohol intermediates were activated by tosylation or chlorination with thionyl chloride.

The heterocyclic alkyl electrophile intermediates were generally worked-up in the following manner. The reaction medium was concentrated under vacuum, the crude concentrate was partitioned between methylene chloride ($CH_2Cl_2$) or chloroform ($CHCl_3$) (50 ml) and water (50 ml), the aqueous layer was extracted with additional organic solvent, the combined organic extracts were washed with water (50 ml), brine (30 ml), and the organic layer was dried over sodium sulfate ($Na_2SO_4$).

The heterocyclic alkyl electrophile intermediates of type (10) were usually purified by column chromatography using the following solvent systems:

A = chloroform;
B = chloroform-methanol-triethylamine, 19:1:0.1;
C = chloroform-methanol-triethylamine, 80:1:0.1;
D = chloroform-methanol, 19:1; E = chloroform-methanol, 40:1;
F = hexane-ethyl acetate-triethylamine, 4:1:0.1;
G = hexane-ethyl acetate-triethylamine, 5:1:0.1;
H = hexane-ethyl acetate-triethylamine, 5:5:0.1;
I = hexane-ethyl acetate-ammonium hydroxide, 3:1:0.1;
J = hexane-ethyl acetate, 1:1;
K = hexane-ethyl acetate, 3:1;
L = hexane-ethyl acetate, 7:1.

The purity of the heterocyclic alkyl electrophile intermediates was confirmed by thin layer chromatography (TLC) analysis. The structure of the heterocyclic alkyl electrophile intermediates was confirmed by $^1H$ NMR analysis wherein the characteristic resonances of the heterocyclic moiety were compared to the characteristic resonances of the immediate precursor. Usually two prominent triplets were observed at approximately 3.70 ppm (heterocycle-$CH_2CH_2X$) and at approximately 4.20 ppm (heterocycle-$CH_2CH_2X$). These heterocyclic alkyl electrophile intermediates were used directly in the synthesis of the compounds of the present invention without further characterization.

The pertinent data for each heterocyclic alkyl electrophile intermediate is presented below in the following format after each general method: (heterocyclic alkyl electrophile precursor, source of precursor, % yield, letter designation for column chromatography solvent system).

Sodium pieces (0.79 g, 34.3 mmol were dissolved in absolute ethanol (150 ml) and the resulting solution was cooled to room temperature. A quantity of 3,5-diethoxycarbonyl-1H-pyrazole (7.3 g, 34.3 mmol, Makabe et al., *Bull. Chem. Soc. Jpn.*, 1975, 48, p. 3210) was added in one portion to the solution and the reaction mixture was stirred at room temperature for 20 minutes. A quantity of 1,2-dibromoethane (34.3 ml, 69.6 mmol) was then added to the solution in one portion and the reaction mixture was heated under reflux for 24 hours. The reaction mixture was then cooled and concentrated under vacuum and the residue worked-up as described above. The intermediate was purified by column chromatography 400 g fine silica; chloroform-methanol, 40:1) to yield 3.9 g (31%) of 2-(3,5-diethoxycarbonyl-1H-pyrazol-1-yl ethyl) bromide.

EXAMPLE 5

This Example illustrates the preparation of halogenated heterocyclic alkyl electrophile intermediate compounds in sodium ethoxide in ethanol.

When an equivalent amount of 4,5-diethoxycarbonyl-1H-imidazole is substituted for 3,5-diethoxycarbonyl-1H-pyrazole in the procedure of Example 4, 2-(4,5-diethoxycarbonyl-1H-imidazole-1-yl)ethyl bromide is isolated after column chromatography (4,5-diethoxycarbonyl-1H-imidazole, Bauer et al., *Heterocyclic Chem.*, 1964, 1 p. 275, 52%, D).

EXAMPLE 6

This Example illustrates the preparation of halogenated heterocyclic alkyl electrophile intermediate compounds in sodium ethoxide in ethanol.

When an equivalent amount of 1,2,4-triazole is substituted for 3,5-diethoxycarbonyl-1H-pyrazole and an equivalent amount of 2-bromochloroethane is substituted for 1,2-dibromoethane in the procedure of Example 4 2-(-H-triazol-1-yl)ethyl chloride is isolated 1,2,4-triazole, Aldrich, 43%, used directly after workup).

EXAMPLE 7

This Example illustrates the preparation of halogenated heterocyclic alkyl electrophile intermediate compounds in sodium ethoxide in ethanol.

When an equivalent amount of 5-phenyl-2H-tetrazole is substituted for 3,5-diethoxycarbonyl-1H-pyrazole and an equivalent amount of 2-bromochloroethane is substituted for 1,2-dibromoethane in the procedure of Example 4, 2-(5-phenyl-2H-tetrazole)ethyl chloride is isolated after column chromatography (5-phenyl-2H-tetrazole, Gump et al., U.S. Pat. No. 2,533,243; *Chem. Abstr.*, 1950, 45, 4271c, 48% from ethanol, mp. 52°–56° C.)

EXAMPLE 8

This Example illustrates the preparation of halogenated heterocyclic alkyl electrophile intermediate compounds in sodium ethoxide in ethanol.

When an equivalent amount of 5-(1-morpholinyl)-2H-tetrazole is substituted for 3,5-diethoxycarbonyl-1H-pyrazole and an equivalent amount of 2-bromochloroethane is substituted for 1,2-dibromoethane in the procedure of Example 4, 2-(5-(1-morpholinyl-2H-tetrazol-2-yl)ethyl chloride is isolated after column chromatography (5-(1-morpholinyl)-2H-tetrazole, Maybridge, 45%).

EXAMPLE 9

This Example illustrates the preparation of halogenated heterocyclic alkyl electrophile intermediate compounds in sodium ethoxide in ethanol.

When an equivalent amount of 1-methyl-5-(2-chloroethylthio)-1H-tetrazole is substituted for 3,5-diethoxycarbonyl-1H-pyrazole and an equivalent amount of 2-bromochloroethane is substituted for 1,2-dibromoethane in the procedure of Example 4, 2-(1-methyl-5-(2-chloroethylthio)-1H-tetrazol-5-yl)ethyl chloride is isolated after column chromatography 1-methyl-5-(2-chloroethylthio)-1H-tetrazole, Aldrich, 59%, A).

EXAMPLE 10

This Example illustrates the preparation of halogenated heterocyclic alkyl electrophile intermediate compounds in sodium ethoxide in ethanol.

When an equivalent amount of 5-methylthio-1,3,4-thiadiazol-5-thione is substituted for 3,5-diethoxycarbonyl-1H-pyrazole and an equivalent amount of 2-bromochloroethane is substituted for 1,2-dibromoethane in the procedure of Example 4, 2-(5-methylthio-1,3,4-thiadiazol-2-yl)thioethyl chloride is isolated after column chromatography (5-methylthio-1,3,4-thiadiazol-5-thione, Umfpathy et al., *Synth. React. Inorg. Met.-Org. Chem.*, 1986, 16, p. 1289, 41%, C).

EXAMPLE 11

This Example illustrates the preparation of halogenated heterocyclic alkyl electrophile intermediate compounds in sodium ethoxide in ethanol.

When an equivalent amount of 5-phenyl-1,3,4-oxadiazole-5-thione is substituted for 3,5-diethoxycarbonyl-1H-pyrazole and an equivalent amount of 2-bromochloroethane is substituted for 1,2-dibromoethane in the procedure of Example 4, 2-(2,3-dihydro-2-thioxo-5-phenyl-1,2,4-oxadiazol-3-yl)ethyl chloride is isolated after column chromatography (5-phenyl-1,3,4-oxadiazole-5-thione, El-Barbary et al., *Chem. Acta.* 1985, 58, p. 71, 59%, ethyl acetate then methanol).

EXAMPLE 12

This Example illustrates the preparation of halogenated heterocyclic alkyl electrophile intermediate compounds in sodium hydride in dimethylformamide.

Sodium hydride (3.9 g, mmol, 50% mineral oil dispersion) was washed with hexane to remove mineral oil (3×10 ml) under a stream of nitrogen. A solution of 1,3-benzoxazolin-2-one (Aldrich, 10 g, 74 mmol) in dimethylformamide (DMF) (70 ml) was then added dropwise with stirring to the hydride until hydrogen evolution ceased. The reaction flask was immersed in an ice bath and 2-bromochloroethane (12.3 ml, 148 mmol) in dimethylformamide (30 ml) was added dropwise. The reaction mixture was stirred at room temperature for 30 minutes, then heated to reflux for 3 days. At the end of this time thin layer chromatography analysis showed consumption of starting material. The reaction mixture was then cooled and the solvent evaporated under vacuum. The residue was worked-up as described above and purified by column chromatography (400 g fine silica, chloroform-methanol-ammonium hydroxide, 80:1:0.1) to yield 11.7 g (80%) of pure 2-(2-oxo-1,3-benzoxazolin-3-yl)ethyl chloride (mp. 77°–79° C. as a pale orange solid.

EXAMPLE 13

This Example illustrates the preparation of halogenated heterocyclic alkyl electrophile intermediate compounds in sodium hydride in dimethylformamide.

When an equivalent amount of 1-ethyl-2-imidazolone is substituted for 1,3-benzoxazolin-2-one and an equivalent amount of 1,2-dibromoethane is substituted for 2-bromochloroethane in the procedure of Example 12, 2-(3-ethyl-2,2-dihydro-2-oxo-1H-imidazol-1-yl)ethyl bromide is isolated after column chromatography (1-ethyl-2-imidazolone, Cortes et al., *J. Org. Chem.*, 1983, 48, p. 2246, 17%, A).

EXAMPLE 14

This Example illustrates the preparation of halogenated heterocyclic alkyl electrophile intermediate compounds in sodium hydride in dimethylformamide.

When an equivalent amount of 1-ethyl-2,4-quinazolinedione is substituted for 1,3-benzoxazolin-2-one and an equivalent amount of 1,2-dibromoethane is substituted for 2-bromochloroethane in the procedure of Example 12, 2-(1-ethyl-1,2,3,4-tetrahydro-2,4-dioxo-3H-quinazolin-3-yl)ethyl bromide is isolated after column chromatography (1-ethyl-2,4-quinazolinedione, Das et al., *J. Indian Chem.*, 1963, 40, p. 35, 55%, crystallized from methylene chloride).

EXAMPLE 15

This Example illustrates the preparation of halogenated heterocyclic alkyl electrophile intermediate compounds in sodium hydride in dimethylformamide.

When an equivalent amount of 2-pyrrolecarboxaldehyde is substituted for 1,3-benzoxazolin-2-one in the procedure of Example 12, 2-(2-formyl-1H-pyrrol-1-yl)ethyl chloride is isolated after column chromatography (2-pyrrolecarboxaldehyde, Aldrich, 48%, I).

EXAMPLE 16

This Example illustrates the preparation of halogenated heterocyclic alkyl electrophile intermediate compounds in sodium hydride in dimethylformamide.

When an equivalent amount of 3-ethyluracil is substituted for 1,3-benzoxazolin-2-one in the procedure of Example 12, 2-(1,2,3,4-tetrahydro-2,4-dioxo-3-ethylpyrimidin-1-yl)ethyl chloride is isolated after column chromatography (3-ethyluracil, Pogolotti et al., *J. Pharm. Sci.*, 1972, 61, p. 1423, 60%, C).

EXAMPLE 17

This Example illustrates the preparation of halogenated heterocyclic alkyl electrophile intermediate compounds in sodium hydride in dimethylformamide.

When an equivalent amount of oxindole is substituted for 1,3-benzoxazolin-2-one in the procedure of Example 12, 2-(2,3-dihydo-2-oxo-1H-indol-1-yl)ethyl chloride is isolated after column chromatography (oxindole, Aldrich, 15%, L).

EXAMPLE 18

This Example illustrates the preparation of halogenated heterocyclic alkyl electrophile intermediate compounds in sodium hydride in dimethylformamide.

When an equivalent amount of 1,4-benzothiazin-3(4H)-one is substituted for 1,3-benzoxazolin-2-one in the procedure of Example 12, 2-(2,3-dihydro-3-oxo-4H-1,3-benzothiazin-4-yl)ethyl chloride is isolated after column chromatography (1,4-benzothiazin-3(4H)-one, Aldrich, 8%, G).

EXAMPLE 19

This Example illustrates the preparation of halogenated heterocyclic alkyl electrophile intermediate compounds in the presence of phase transfer catalysts.

A solution of 1-ethoxycarbonyl-2H-indazolin-3-one (Wyrick et al., *J. Med. Chem.*, 1984, 27, 768) (3 g, 14.5 mmol) in tetrahydrofuran-dimethylformamide (THF-DMF) (25:5, ml) was added in one portion to a stirred suspension of 1,2-dibromoethane (4.2 g, 29 mmol), crushed potassium hydroxide (KOH) (1.1 g, 16.7 mmol, 85.5%), tetrabutylammonium bromide (1.4 g, 4.4 mmol), and tetrahydrofuran (5 ml). The reaction mixture was heated under reflux for 3 days at which time thin layer chromatography analysis showed the absence of starting material and the emergence of two new spots. The product was worked-up as described above. The crude product was purified by gradient elution column chromatography (200 g fine silica; hexane-ethyl acetate, 7:1, to elute the first component; then 3:1 to 1:1 of the solvent system to elute the second component). The first component was identified spectroscopically as 3-(2-chloroethoxy)-1-ethoxycarbonyl-1H-indazole (2.2 g, 56%; Rf 0.34, hexaneethyl acetate, 3:1) and the second component was identified spectroscopically as 1-ethoxycarbonyl-2-(2-chloroethyl)-2H-indazolin-3-one (0.6 g, 15%; Rf 0.16). The first component was employed to prepare compounds of the present invention.

EXAMPLE 20

This Example illustrates the preparation of halogenated heterocyclic alkyl electrophile intermediate compounds in the presence of phase transfer catalysts.

When an equivalent amount of pyrithyldione is substituted for 1-ethoxycarbonyl-2H-indazolin-3-one in the procedure of Example 19 using tetrahydrofuran as solvent, 2-(1,2,3,4-tetrahydro-2,4-dioxo-3,3-diethyl-pyridin-1-yl)ethyl bromide is isolated after column chromatography(pyrithyldione, Aldrich, 52%, F).

EXAMPLE 21

This Example illustrates the preparation of halogenated heterocyclic alkyl electrophile intermediate compounds in the presence of phase transfer catalysts.

When an equivalent amount of 5-isopropyl-1,2,4-triazolin-6-one is substituted for 1-ethoxycarbonyl-2H-indazolin-3-one in the procedure of Example 19 using toluene as solvent, 2-(1,6-dihydro-5-isopropyl-6-oxo-1,2,4-triazin-1-yl)ethyl bromide is isolated after column chromatography (5-isopropyl-1,2,4-triazolin-6-one, Taylor et al., *J. Heterocyclic Chem.*, 1985, 22, p. 409, 49%, J.)

EXAMPLE 22

This Example illustrates the preparation of halogenated heterocyclic alkyl electrophile intermediate compounds in the presence of phase transfer catalysts.

When an equivalent amount of 1,8-naphthalene is substituted for 1-ethoxycarbonyl-2H-indazolin-3-one in the procedure of Example 19 using benzene as solvent, 2-(N-(1,8-naphthalenecarboxamidyl)ethyl bromide is isolated after column chromatography (1,8-naphthalene, Aldrich, 18%, C).

EXAMPLE 23

This Example illustrates the preparation of halogenated heterocyclic alkyl electrophile intermediate compounds in the presence of phase transfer catalysts.

When an equivalent amount of 3-methylpyrazole is substituted for 1-ethoxycarbonyl-2H-indazolin-3-one and 2-bromochloroethane is substituted for 1,2-dibromoethane in the procedure of Example 19 using toluene as solvent, 2-(3-methyl-1H-pyrazol-1-yl)ethyl chloride is isolated after column chromatography (3-methylpyrazole, Aldrich, 36%, C).

EXAMPLE 24

This Example illustrates the preparation of halogenated heterocyclic alkyl electrophile intermediate compounds in the presence of phase transfer catalysts.

When an equivalent amount of 3,5-dimethylpyrazole is substituted for 1-ethoxycarbonyl-2H-indazolin-3-one and 2-bromochloroethane is substituted for 1,2-dibromoethane in the procedure of Example 19 using tetrahydrofuran as solvent, 2-(3,5-dimethyl-1H-pyrazol-1-yl)ethyl chloride is isolated after column chromatography (3,5-dimethylpyrazole, Aldrich, 24%, C).

EXAMPLE 25

This Example illustrates the preparation of halogenated heterocyclic alkyl electrophile intermediate compounds in the presence of phase transfer catalysts.

When an equivalent amount of 4-iodopyrazole is substituted for 1-ethoxycarbonyl-2H-indazolin-3-one and 2-bromochloroethane is substituted for 1,2-dibromoethane in the procedure of Example 19 using toluene as solvent, 2-(4-iodo-1H-pyrazol-1-yl)ethyl chloride is isolated after column chromatography (4-iodopyrazole, Aldrich, 41%, C).

EXAMPLE 26

This Example illustrates the preparation of halogenated heterocyclic alkyl electrophile intermediate compounds in the presence of phase transfer catalysts.

When an equivalent amount of 1-phenyl-3(2H)-pyrazolinone is substituted for 1-ethoxycarbonyl-2H-indazolin-3-one and 2-bromochloroethane is substituted for 1,2-dibromoethane in the procedure of Example 19 using tetrahydrofuran as solvent, 2-(2,3,4,5-tetrahydro-2-phenyl-5-oxo-1H-pyrazol1-yl)ethyl chloride is isolated after column chromatography (1-phenyl-3(2H)-pyrazolinone, Aldrich, 79%, J).

EXAMPLE 27

This Example illustrates the preparation of halogenated heterocyclic alkyl electrophile intermediate compounds in the presence of phase transfer catalysts.

When an equivalent amount of 1-phenyl-3(2H)-pyrazolinone is substituted for 1-ethoxycarbonyl-2H-indazolin-3-one and 2-bromochloroethane is substituted for 1,2-dibromoethane in the procedure of Example 19 using tetrahydrofuran as solvent, 2-(2,3,4,5-tetrahydro-2-phenyl-5-oxo-1H-pyrazol-1-yl)ethyl chloride is isolated after column chromatography (1-phenyl-3(2H)-pyrazolinone, Aldrich, 79%, J).

EXAMPLE 28

This Example illustrates the preparation of halogenated heterocyclic alkyl electrophile intermediate compounds in the presence of phase transfer catalysts.

When an equivalent amount of 3-ethyl-3-phenyl-glutarimide is substituted for 1-ethoxycarbonyl-2H-indazolin-3-one and 2-bromochloroethane is substituted for 1,2-dibromoethane in the procedure of Example 19 using tetrahydrofuran as solvent, 2-(2,6-dioxo-3-ethyl-3-phenylpiperidin-1-yl) ethyl chloride is isolated after column chromatography (3-ethyl-3-phenylglutarimide, Tagmann, E. A. *Helv. Chim. Acta*, 1952, 35, p. 1541, 84%, C).

EXAMPLE 23

This Example illustrates the preparation of halogenated heterocyclic alkyl electrophile intermediate compounds in the presence of phase transfer catalysts.

When an equivalent amount of 4-pyrimidone is substituted for 1-ethoxycarbonyl-2H-indazolin-3-one and 2-bromochloroethane is substituted for 1,2-dibromoethane in the procedure of Example 19, 2-(1,6-dihydro-6-oxopyrimidin-1-yl)ethyl chloride is isolated after column chromatography (4-pyrimidone, Aldrich, 34%, B).

EXAMPLE 30

This Example illustrates the preparation of halogenated heterocyclic alkyl electrophile intermediate compounds in the presence of phase transfer catalysts.

When an equivalent amount of 2-methylthio-5-methyl-1,3-pyrimidin-6-one is substituted for 1-ethoxycarbonyl-2H-indazolin-3-one and 2-bromochloroethane is substituted for 1,2-dibromoethane in the procedure of Example 19 using tetrahydrofuran as solvent, 2-(2-methylthio-1,6-dihydro-4-oxo-5-methylpyrimidin-1-yl)ethyl chloride is isolated after column chromatography (2-methylthio-5-methyl-1,3-pyrimidin-6-one, Spengler et al., *Arch. Pharm. (Weinheim)*. 1984, 317, p. 425, 26%, J).

EXAMPLE 31

This Example illustrates the preparation of halogenated heterocyclic alkyl electrophile intermediate compounds in the presence of phase transfer catalysts.

When an equivalent amount of 3-ethyl-2-benzimidazolinone is substituted for 1-ethoxycarbonyl-2H-indazolin-3-one and 2-bromochloroethane is substituted for 1,2-dibromoethane in the procedure of Example 19 using tetrahydrofuran as solvent, 2-(3-ethyl-2,3-dihydro-2-oxo-1H-benzimidazol1-yl)ethyl chloride is isolated after column chromatography (3-ethyl-2-benzimidazolinone, Aldrich, 6%, A).

EXAMPLE 32

This Example illustrates the preparation of tosylated heterocyclic alkyl electrophile intermediate compounds from alcohols.

Triethylamine (4.2 ml, 30 mmol was added, in one portion, and then, in portions, para-toluenesulfonyl chloride (5.7 g, 30 mmol was added, to a solution of 2-hydroxymethyl-1,4-benzodioxane (Maybridge, 5 g, 30 mmol) in methylene chloride (50 ml). A mild exothermic reaction ensued. The reaction mixture was stirred overnight. Precipitated triethylamine hydrochloride was separated by filtration and washed with methylene chloride (50 ml). The organic medium was washed with 10% aqueous hydrochloric acid (50 ml , water 50 ml , brine (30 ml), and dried over sodium sulfate. Purification of the crude product by column chromatography (400 g fine silica, hexane-ethyl acetatetriethylamine; 100:100:1) yielded pure (1,4-benzodioxan-2-yl)methyl tosylate (66%).

EXAMPLE 33

This Example illustrates the preparation of tosylated heterocyclic alkyl electrophile intermediate compounds from alcohols.

When an equivalent amount of 2-(2-hydroxyethyl)-2,3-dihydro-3(2H)-isoindolinone is substituted for 2-hydroxymethyl-1,4-benzodioxane in the procedure of Example 32, 2-(1,3-dihydro-1-oxo-2H-isoindol-2-yl)ethyl tosylate is isolated after column chromatography (2-(2-hydroxyethyl)-2,3-dihydro-3(2H)-iso-indolinone, Minaskanian et al., Eur. Pat. Appl. EP 194685 A1 1986); *Chem. Abstr.*, 1986, 106, 4894z, 66%, mp. 75°-77.5 C., from ether).

EXAMPLE 34

This Example illustrates the preparation of chlorinated heterocyclic alkyl electrophile intermediate compounds from alcohols.

Thionyl chloride ($SOCl_2$, 6.2 ml) in chloroform (15 ml) was added dropwise to an ice chilled solution of 2-(2-hydroxyethyl)pyridine (Aldrich, 10 g, 81 mmol in chloroform (10 ml . After addition was complete, the reaction mixture was stirred for 15 hours. The solvent and excess thionyl chloride were removed on a vacuum rotary evaporator followed by exposure to high vacuum (90 minutes, 0.5 mm Hg, 80° C.) Recrystallization of the crude brown solid from isopropanol-isopropyl ether yielded 10.8 g of pure 2-(2-pyridinyl)ethyl chloride hydrochloride (mp. 124°-125° C., lit. mp., about 120° C., Gump et al., U.S. Pat. No. 2,533,243; *Chem. Abstr.*, 1950, 45, p. 4271c) as light tan beads.

EXAMPLE 35

This Example illustrates the preparation of chlorinated heterocyclic alkyl electrophile intermediate compounds from alcohols.

When an equivalent amount of 4-methyl-5-(2-hydroxyethyl)thiazole is substituted for 2-(2-hydroxyethyl) pyridine in the procedure of Example 34 using benzene as solvent, 2-(4-methylthiazol-5-yl)ethyl chloride hydrochloride is isolated after column chromatography (4-methyl-5-(2-hydroxyethyl)thiazole, Aldrich, 71%, mp. 135°-137° C., from isopropanol).

EXAMPLE 36

This Example illustrates the preparation of chlorinated heterocyclic alkyl electrophile intermediate compounds from alcohols.

When an equivalent amount of 3-(2-hydroxyethyl)-pyridine is substituted for 2-(2-hydroxyethyl)pyridine in the procedure of Example 34, 2-(3-pyridinyl)ethyl chloride hydrochloride is isolated after column chromatography (3-(2-hydroxyethyl)pyridine, Tamura et al., *Synthesis*, 1977, p. 1, 65%, mp. 154°–155° C.).

EXAMPLE 37

This Example illustrates the preparation of compounds of the present invention.

In general, the compounds of the present invention were prepared by reacting a secondary amine intermediate compound of type 9 from Example 1 (about 1 g) with a 10% excess of a heterocyclic alkyl electrophile intermediate compound of type 10 from Examples 2–36 in the presence of an equivalent amount of sodium carbonate (about 1.5 g) and a catalytic amount of sodium iodide (about 100 mg) in refluxing acetonitrile. When the electrophile intermediate compound was an alpha-haloketone, the reaction was generally carried out at room temperature. Completion of the reaction was determined by the absence of starting material according to thin layer chromatography analysis. The reaction mixture was then filtered free of insoluble materials and the filtrate was concentrated under vacuum. The crude concentrate was partitioned between 10% aqueous hydrochloric acid (40 ml) and ether (40 ml). The acidic aqueous layer was extracted with additional ether and then made alkaline with 6N aqueous sodium hydroxide. The liberated free base was extracted with methylene chloride (2×40 ml) and the organic extract was washed with water (50 ml), brine (30 ml), and dried over sodium sulfate. The crude product was purified by column chromatography over fine silica and eluting with chloroform-methanol-ammonium hydroxides.

EXAMPLES 38–42

This Example illustrates the preparation of amino alcohol compounds of the present invention.

A quantity of sodium borohydride ($NaBH_4$, 100 mg) was added to a stirred solution of the appropriate aminoketone (2 mmol) in absolute ethanol (10 ml). Thin layer chromatography analysis of the reaction mixture generally showed complete reaction after 30 minutes of stirring at room temperature. The reaction mixture was then concentrated under vacuum and worked-up as described above. The crude product was purified by column chromatography over fine silica using the solvent system chloroform-methanol-ammonium hydroxide.

The following amino alcohol compounds of the present invention were prepared by the above procedure:

N-(phenyl)-N-[1-(2-hydroxy-2-(2-thienyl)ethyl)-4-methoxycarbonyl-4-piperidinyl]propanamide N-(phenyl)-N-[1-(2-hydroxy-2-(2-thienyl)ethyl)-4-methoxymethyl-4-piperidinyl]propanamide N-(phenyl)-N-[1-(1-methyl-2-hydroxy-2-(2-thienyl)-ethyl)-4-methoxymethyl-4-piperidinyl]propanamide N-(phenyl)-N-[1-(2-hydroxy-2-(2-furanyl)ethyl)-4-methoxymethyl-4-piperidinyl]propanamide N-(phenyl)-N-[1-(2-hydroxy-2-(5-methyl-2-furanyl)-ethyl)-4-methoxymethyl-4-piperidinyl]propanamide

EXAMPLE 43

This Example illustrates a general procedure for preparing compounds of the present invention.

A mixture of the appropriate secondary amine intermediate compound of type 9 from Example 1 (Van Daele et al., *J. Arzneim-Forsch. Drug Res.*, 1976, 26, p. 1521) (1.15 g, 4.2 mmol), 4-vinylpyridine (0.67 g, 6.3 mmol), and 2-methoxyethanol (10 ml) was stirred under reflux overnight. At the end of this period, thin layer chromatography analysis of the reaction mixture showed complete reaction. The reaction was then concentrated under vacuum and the crude concentrate was partitioned between 10% aqueous hydrochloric acid (40 ml and ether (40 ml). The acidic aqueous layer was extracted with additional ether and then made alkaline with 6N aqueous sodium hydroxide. The liberated free base was extracted with methylene chloride (2×40 ml) and the organic extract was washed with water (50 ml), brine (30 ml) and dried over sodium sulfate. The crude product was purified by column chromatography (135 g fine silica; chloroform-methanol-ammonium hydroxide; 40:1:0.01 to elute the faster, excess 4-vinylpyridine; followed by flash chromatography; same column; chloroform-methanol-ammonium hydroxide; 30:1:0.1 to yield pure N- phenyl)-N-[1-(2-(4-pyridinyl)ethyl)-4-methoxymethyl-4-piperidinyl]-propanamide (1.22 g, 74%) as a golden oil.

EXAMPLE 44

This Example illustrates a general procedure for preparing compounds of the present invention.

A mixture of the appropriate secondary amine intermediate compound of type 9 from Example 1 (Van Daele et al., *J. Arzneim-Forsch. Drug Res.*, 1976, 26, p. 1521) (0.94 g, 3.2 mmol , 3-(dimethylaminomethyl)-1H-indole (0.62 g, 3.6 mmol), NaI (about 100 mg), and 2-methoxyethanol (9 ml) was stirred under reflux for 2 hours. A prominent odor of dimethylamine was detected. At the end of this period, thin layer chromatography analysis of the reaction mixture showed completion of the reaction. The reaction was then concentrated under vacuum and the crude concentrate was partitioned between 10% aqueous hydrochloric acid (40 ml) and ether (40 ml). The acidic aqueous layer was extracted with additional ether and then made alkaline with 6N aqueous sodium hydroxide. The liberated free base was extracted with methylene chloride (2×40 ml) and the organic extract was washed with water (50 ml), brine (30 ml , and dried over sodium sulfate. The crude product was purified by flash column chromatography (100 g fine silica; chloroform-methanol-ammonium hydroxide, 30:1:0.01 to 20:1:0.1) to Yield pure N-(phenyl)-N-[1-(1H-indol-3-yl(methyl))-4-methoxy-carbonyl-4-piperidinyl]propanamide (0.95 g, 70%) as a cream colored solid.

EXAMPLE 45

This Example illustrates a general procedure for preparing compounds of the present invention having an $R_2$ clonidine substituent.

A mixture of 4-methoxycarbonyl-4-(N'-phenylpropionamido)piperidine (7.34 g, 25 mmol), 2-bromoethanol (3.96 g, 32 mmol), sodium carbonate (20.0 g, 189 mmol), and sodium iodide (1.0 g) in acetonitrile (200ml) was heated to reflux for three days. The reaction mixture was cooled and filtered. The filtrate was concentrated under vacuum yielding an oily residue. The residue was chromatographed on silica gel (250 g; ethyl acetate/hexane; 1:4) to yield 1-(2-hydroxyethyl)-4-methoxycarbonyl-4-(N'-phenylpropionamido)piperidine (8.1 g, 96%) as an oil.

A solution of methanesulfonyl chloride 0.374 g, 3.3 mmol in ethyl acetate (3ml was added to a mixture of 1-(2-hydroxyethyl)-4-methoxycarbonyl-4-(N'-phenylpropionamido) piperidine (1.0 g, 3 mmol) and triethylamine. The resulting mixture was stirred overnight. The reaction mixture was filtered and the filtrate was concentrated under vacuum to give an oily residue. The residue was chromatographed on silica gel (290 g; ethyl acetate/hexane: 1:4) to yield 1-(2-methanesulfonylethyl)-4-methoxycarbonyl-4-(N'-phenyl-propionamido)-piperidine (0.53 g, 43%) as an oil.

A mixture of 1-(2-methanesulfonylethyl)-4-methoxycarbonyl-4-(N'-phenylpropionamido)piperidine (0.50 g,1.2 mmol), clonidine hydrochloride (0.323 g, 1.2 mmol), and sodium carbonate (1.0 g, 9.4 mmol) in ethyl acetate (10ml) was heated to reflux for three days. The mixture was cooled and filtered and the filtrate was evaporated under vacuum to give an oily residue. The residue was chromatographed on silica gel (25 g; ethyl acetate/methanol; 4:1; 5% ammonium hydroxide in methanol) to yield 1-[2-(2,6-di-chloroanilineO-2-imidazolin-1-yl]-ethyl-4-[N-phenylpropionamido]-4-methoxycarbonyl-piperidine as a crystalline solid (0.448 g, 68%), m.p. 75° C.

EXAMPLES 46-98

Further examples of compounds within the scope of the present invention which may be prepared by procedures analogous to those described above include:

N-(phenyl)-N-[1-(2-(1H-pyrrol-1-yl)ethyl)-4-methoxycarbonyl-4-piperidinyl]propanamide
N-(phenyl)-N-[1-(2-(2-formyl-1H-pyrrol-1-yl)-ethyl)-4-methoxycarbonyl-4-piperidinyl]-propanamide
N-(phenyl)-N-[1-(2-(1H-pyrazol-1-yl)ethyl)-4-methoxycarbonyl-4-piperidinyl]propanamide
N-(phenyl)-N-[1-(2-(3-methyl-1H-pyrazol-1-yl)-ethyl)-4-methoxycarbonyl-4-piperidinyl]-propanamide
N-(phenyl)-N-[1-(2-(3,5-dimethyl-1H-pyrazol-1-yl)-ethyl)-4-methoxycarbonyl-4-piperidinyl]-propanamide
N-(phenyl)-N-[1-(2-(4-iodo-1H-pyrazol-1-yl)-ethyl)-4-methoxycarbonyl-4-piperidinyl]propanamide
N-(phenyl)-N-[1-(2-(3,5-diethoxycarbonyl-1H-pyrazol-1-yl)ethyl)-4-methoxycarbonyl-4-piperidinyl]-propanamide
N-(phenyl)-N-[1-(2-(1H-imidazol-1-yl)ethyl)-4-methoxycarbonyl-4-piperidinyl]propanamide
N-(phenyl)-N-[1-(2-(5-nitro-1H-imidazol-1-yl)-ethyl)-4-methoxycarbonyl-4-piperidinyl]-propanamide
N-(phenyl)-N-[1-(2-(2-methyl-5-nitro-1H-imidazol-1-yl)-ethyl)-4-methoxycarbonyl-4-piperidinyl]-propanamide
N-(phenyl)-N-[1-(2-(4,5-diethoxycarbonyl-1H-imidazol-1-yl)-ethyl)-4-methoxycarbonyl-4-piperidinyl]-propanamide
N-(phenyl)-N-[1-(2-(1H-imidazol-4-yl)ethyl)-4-methoxycarbonyl-4-piperidinyl]propanamide
N-(phenyl -N-[1-(2-(1-methyl-1H-imidazol-2-yl)-ethylthio)-4-methoxycarbonyl-4-piperidinyl]-propanamide
N-(phenyl)-N-[1-(2-(1H-triazol-1-yl)ethyl)-4-methoxycarbonyl-4-piperidinyl]propanamide
N-(phenyl)-N-[1-(2-(2H-tetrazol-2-yl)ethyl)-4-methoxycarbonyl-4-piperidinyl]propanamide
N-(phenyl)-N-[1-(2-(5-phenyl-2H-tetrazol-2-yl)-ethyl)-4-methoxycarbonyl-4-piperidinyl]-propanamide
N-(phenyl)-N-[1-(2-(1-methyl-1H-tetrazol-5-yl)-ethylthio)-4-methoxycarbonyl-4-piperidinyl]-propanamide
N-(phenyl)-N-[1-(2-oxo-2-(2-thienyl)ethyl)-4-methoxycarbonyl-4-piperidinyl]propanamide
N-(phenyl)-N-[1-(2-hydroxy-2-(2-thienyl)ethyl)-4-methoxycarbonyl-4-piperidinyl]propanamide
N-(phenyl)-N-[1-(2-(2,3,4,5-tetrahydro-2-oxo-oxazol-3-yl)ethyl)-4methoxycarbonyl-4-piperidinyl]-propanamide
N-(phenyl)-N-[1-(2-(2,3,4,5-tetrahydro-2-phenyl-5oxo-1H-pyrazol-1-yl)-ethyl)-4-methoxycarbonyl-4-piperidinyl]propanamide
N-(phenyl)-N-[1-(2-(2,3,4,5-tetrahydro-2,4-dioxo-5-methyl-5-phenyl-1H-imidazol-3-yl)ethyl)-4-methoxycarbonyl-4-piperidinyl]propanamide
N-(phenyl)-N-[1-(2-(5-methylthio-1,3,4-thiadiazol-2-yl)ethylthio)-4-methoxycarbonyl-4-piperidinyl]-propanamide
N-(phenyl)-N-[1-(2-(2,3-dihydro-2-thioxo-5-phenyl-1,3,4-oxadiazol-3-yl)-ethyl)-4-methoxycarbonyl-4-piperidinyl]propanamide
N-(phenyl)-N-[1-(2-(1,2,3,4-tetrahydro-2,4-dioxo-3,3-diethylpyridin-1-yl)-ethyl)-4-methoxycarbonyl-4-piperidinyl]propanamide
N-(phenyl)-N-[1-(2-(2,6-dioxo-3-ethyl-3-phenylpiperidin-1-yl)ethyl)-4-methoxycarbonyl-4-piperidinyl]-propanamide
N-(phenyl)-N-[1-(2-(1,6-dihydro-6-oxo-pyrimidin-1-yl)ethyl-4-methoxycarbonyl-4-piperidinyl]-propanamide
N-(phenyl)-N-[1-(2-(2-methylthio-1,6-dihydro-4-oxo-5-methylpyrimidin-1-yl)ethyl)-4-methoxycarbonyl-4-piperidinyl]propanamide
N-(phenyl)-N-[1-(2-(1,2,3,4-tetrahydro-2,4-dioxo-3-ethylpyrimidin-1-yl)-ethyl)-4-methoxycarbonyl-4-piperidinyl]propanamide
N-(phenyl)-N-[1-(2-(1,6-dihydro-6-oxo-3-methylpyridazin-1-yl)ethyl)-4-methoxycarbonyl-4-piperidinyl]-propanamide
N-(phenyl)-N-[1-(2-(1,6-dihydro-3-(2-propyl)-6-oxo-1,2,4-triazin-1-yl)-ethyl)-4-methoxycarbonyl-4-piperidinyl]propanamide
N-(phenyl)-N-[1-(1H-indol-3-yl(methyl))-4-methoxycarbonyl-4-piperidinyl]propanamide
N-(phenyl)-N-[1-(2-(2,3-dihydro-2-oxo-1H-indol-1-yl)ethyl)-4-methoxycarbonyl-4-piperidinyl]propanamide
N-(phenyl)-N-[1-(2-(3,3-dimethyl-2,3-dihydro-2-oxo-1H-indol-1-yl)ethyl)-4-methoxycarbonyl-4-piperidinyl]propanamide
N-(phenyl) N-[1-(2-(2,3-dihydro-2-oxo-3,3-spiroethane-1H-indol-1-yl)ethyl)-4-methoxycarbonyl-4-piperidinyl]propanamide
N-(phenyl)-N-[1-(2-(1,3-dihydro-1,3-dioxo-2H-isoindol-2-yl)-ethyl)-4-methoxycarbonyl-4-piperidinyl]-propanamide
N-(phenyl)-N-1-(2H-benzimidazol-1-yl(ethyl))-4-methoxycarbonyl-4-piperidinyl]propanamide
N-(phenyl)-N-[1-(0-(1-ethoxycarbonyl-1H-benzopyrazol-3-yl)-ethoxy)-4-methoxycarbonyl-4-piperidinyl]propanamide
N-(phenyl)-N-[1-(2-(3-ethyl-2,3-dihydro-2-oxo-1H-benzimidazol-1-yl)ethyl)-4-methoxycarbonyl-4-piperidinyl]propanamide
N-(phenyl)-N-[1-(2-(2,3-dihydro-2-oxo-benzoxazol-3-yl)ethyl)-4-methoxycarbonyl-4-piperidinyl]-propanamide N-(phenyl)-N-[1-(2-(5-chloro-2,3-dihydro-2-oxo-benzoxazol-3-yl)-ethyl)-4-methoxycarbonyl-4-piperidinyl]-propanamide
N-(phenyl)-N-[1-(2-oxo-2-(2,3-dihydro-2-oxo-benzoxazol-6-yl)ethyl)-4-methoxycarbonyl-4-piperidinyl]-propanamide
N-(phenyl)-N-[1-(7-methoxy-2-oxo-2H-benzopyran-4-yl(methyl))-4-methoxycarbonyl-4-piperidinyl]-propanamide
N-(phenyl)-N-[1-(1,4-benzodioxan-2-yl(methyl))-4-methoxycarbonyl-4-piperidinyl]propanamide
N-(phenyl)-N-[1-(2-(2,3-dihydro-3-oxo-4H-1,3-benzothiazin-4-yl)ethyl))-4 methoxycarbonyl-4-piperidinyl]propanamide
N-(phenyl)-N-[1-(2-(2-methyl-3,4-dihydro-4-oxo-3H-quinazolin-3-yl)ethyl))-4-methoxycarbonyl-4-piperidinyl]propanamide
N-(phenyl)-N-[1-(2-(1,2,3,4-tetrahydro-2,4-dioxo-3H-quinazolin-3-yl)ethyl))-4-methoxycarbonyl-4-piperidinyl]propanamide
N-(phenyl)-N-[1-(2-(1-ethyl-1,2,3,4-tetrahydro-2,4dioxo-3H-quinazolin-3-yl)ethyl))-4-methoxycarbonyl-4piperidinyl]propanamide
N-(phenyl)-N-[1-(2-(1,2,3,6-tetrahydro-1,3-dimethyl-2,6-dioxo-7H-purin-7-yl)ethyl))-4-methoxy-carbonyl-4-piperidinyl]propanamide
N-(phenyl)-N-[1-(2-(1,2,3,6-tetrahydro-3,7-dimethyl-2,6-dioxo-1H-purin-1-yl)ethyl))-4-methoxy-carbonyl-4-piperidinyl]propanamide
N-(phenyl)-N-[1-(2-(N-1,8-naphthalene-sulfamidyl)-ethyl))-4-methoxycarbonyl-4-piperidinyl]-propanamide
N-(phenyl)-N-[1-(2-(N-1,8-naphthalene-dicarboxamidyl)ethyl))-4-methoxycarbonyl-4-piperidinyl]-propanamide
N-(phenyl)-N-[1-(2-(3-thienyl)ethyl)-4-methoxycarbonyl-4piperidinyl]propanamide

EXAMPLES 99–135

Further examples of compounds within the scope of the present invention which may be prepared by procedures analogous to those described above include:
N-(phenyl)-N-[1-(2-(1H-pyrrol-1-yl)ethyl)-4-methoxymethyl-4-piperidinyl]propanamide
N-(phenyl)-N-[1-(2-(2-formyl 1H-pyrrol-1-yl)-ethyl)-4-methoxymethyl-4-piperidinyl]propanamide
N-(phenyl)-N-[1-(2-(1H-pyrazol-1-yl)ethyl)-4-methoxymethyl-4-piperidinyl]propanamide
N-(phenyl)-N-[1-(2-(3,5-dimethyl-1H-pyrazol-1-yl)-ethyl)-4-methoxymethyl-4-piperidinyl]propanamide
N-(phenyl)-N-[1-(2(4-iodo-1H-pyrazol-1-yl)ethyl)-4-methoxymethyl-4-piperidinyl]propanamide
N-(phenyl)-N-[1-(2-(2-methyl-5-nitro-1H-imidazol-1-yl)ethyl)-4-methoxymethyl-4-piperidinyl]-propanamide
N-(phenyl)-N-[1-(2-(1H-imidazol-4-yl)ethyl)-4-methoxymethyl-4-piperidinyl]propanamide
N-(phenyl)-N-[1-(2-(1-methyl-1H-imidazol-2-yl)-ethylthio)-4-methoxymethyl-4-piperidinyl]propanamide
N-(phenyl)-N-[1-(2-(1H-triazol-1-yl)ethyl)-4-methoxymethyl-4-piperidinyl]propanamide
N-(phenyl)-N-[1-(2-(5-trifluoromethyl-4-methyl-4H-triazol-3-yl)-ethylthio)-4 methoxymethyl-4-piperidinyl]propanamide
N-(phenyl)-N-[1-(2-(2H-tetrazol-2-yl)ethyl)-4-methoxymethyl-4-piperidinyl]propanamide
N-(phenyl)-N-[1-(2-(5-morpholinyl-2H-tetrazol-2-yl)-ethyl)-4-methoxymethyl-4-piperidinyl]propanamide
N-(phenyl)-N-[1-(1 methyl-2-oxo-2-(2-thienyl)-ethyl)-methoxymethyl-4-piperidinyl]propanamide
N-(phenyl)-N-[1-(2-hydroxy-2-(2-thienyl)ethyl)-4-methoxymethyl-4-piperidinyl]propanamide
N-(phenyl)-N-[1-(1-methyl-2-hydroxy-2-(2-thienyl)-ethyl)-4-methoxymethyl-4-piperidinyl]propanamide
N-(phenyl)-N-[1-(2-hydroxy-2-(2-furanyl)ethyl)-4-methoxymethyl-4-piperidinyl]propanamide
N-(phenyl)-N-[1-(2-hydroxy-2-(5-methyl-2-furanyl)-ethyl)-methoxymethyl-4-piperidinyl]propanamide
N-(phenyl)-N-[1-(2-(3-ethyl-2,3-dihydro-2-oxo-1H-imidazol-1-yl)-ethyl)-4-methoxymethyl-4-piperidinyl]propanamide N-(phenyl)-N-[1-(2-(2,3,4,5-tetrahydro-2-phenyl-5oxo-1H-pyrazol-1-yl)-ethyl)-4-methoxymethyl-4-piperidinyl]propanamide
N-(phenyl)-N-[1-(2-(1,5-dihydro-3-methyl-4-amino-5-oxo-1H-triazol-1-yl -ethyl)-4-methoxymethyl-4-piperidinyl]propanamide
N-(phenyl)-N-[1-(2-(1,2,3,4-tetrahydro-2,4-dioxo-3,3-diethylpyridin-1-yl)-ethyl)-4-methoxymethyl-4-piperidinyl]propanamide
N-(phenyl)-N-[1-(2-(2-methylthio-1,6-dihydro-4-oxo-5-methylpyrimidin-1-yl)ethyl)-4-methoxymethyl-4-piperidinyl]propanamide
N-(phenyl)-N-[1-(2-(1,2,3,4-tetrahydro-2,4-dioxo-3-ethylpyrimidin-1-yl)-ethyl)-4-methoxymethyl-4-piperidinyl]propanamide
N-(phenyl)-N-[1-(2-(2,3-dihydro-2-oxo-1H-indol-1-yl)-ethyl)-4-methoxymethyl-4-piperidinyl]propanamide
N-(phenyl)-N-[1-(2-(3,3-dimethyl-2,3-dihydro-2-oxo-1H-indol-1-yl)ethyl)-4-methoxymethyl-4-piperidinyl]-propanamide
N-(phenyl)-N-[1-(2-(2,3-dihydro-2-oxo-3,3-spiroethane-1H-indol-1-yl)ethyl)-4-methoxymethyl-4-piperidinyl]propanamide
N-(phenyl)-N-[1-(2-(1,3-dihydro-1-oxo-2H-isoindol-2-yl)ethyl)-4-methoxymethyl-4-piperidinyl]-propanamide
N-(phenyl)-N-[1-(2-(1,3-dihydro-1,3-dioxo-2H-isoindol-2-yl)-ethyl)-4-methoxymethyl-4-piperidinyl]-propanamide
N-(phenyl)-N-[1-(2-(3-ethyl-2,3-dihydro-2-oxo-1H-benzimidazol-1-yl)ethyl)-4-methoxymethyl-4-piperidinyl]propanamide
N-(phenyl)-N-[1-(2-(2,3-dihydro-2-oxo-benzoxazol-3-yl)ethyl)-4-methoxymethyl-4-piperidinyl]-propanamide
N-(phenyl)-N-[1-(2-(2-oxo-2H-benzopyran-7-oxy)ethyl)-4-methoxymethyl-4-piperidinyl]propanamide
N-(phenyl)-N-[1-(1,4-benzodioxan-2-yl(methyl))-4-methoxymethyl-4-piperidinyl]propanamide
N-(phenyl)-N-[1-(5-fluoro-1,3-benzodioxan-8-yl(methyl))-4-methoxymethyl-4-piperidinyl]-propanamide
N-(phenyl)-N-[1-(2-(2-methyl-3,4-dihydro-4-oxo-3H-quinazolin-3-yl)ethyl))-4-methoxymethyl-4-piperidinyl]propanamide
N-(phenyl)-N-[1-(2-(1-ethyl-1,2,3,4-tetrahydro-2,4-dioxo-3H-quinazolin-3-yl)ethyl))-4-methoxymethyl-4-piperidinyl]propanamide
N-(phenyl)-N-[1-(2-(N-1,8-naphthalene-carboxamidyl)-ethyl))-4-methoxymethyl-4-piperidinyl]-propanamide
N-(phenyl)-N-[1-(2-(3-thienyl)ethyl)-4-methoxymethyl-4piperidinyl]propanamide

EXAMPLES 136–156

Further examples of compounds within the scope of the present invention which may be prepared by procedures analogous to those described above include:

N-(2-fluorophenyl)-N-[1-(2-(1H-pyrazol-1-yl)ethyl)-4-methoxycarbonyl-4-piperidinyl]propanamide N-(2-fluorophenyl)-N-[1-(2-(N-phthalimidyl)-ethyl)-4-methoxycarbonyl-4-piperidinyl]propanamide N-(2-fluorophenyl)-N-[1-(2-(N-phthalimidyl)-ethyl)-4-methoxycarbonyl-4-piperidinyl]-2-methoxy-propanamide N-(2-fluorophenyl)-N-[1-(2-(1H-pyrazol-1-yl)ethyl)-4-methoxymethyl-4-piperidinyl]propanamide N-(2-fluorophenyl)-N-[1-(2-(3-ethylbenzimid-azol-1-yl)ethyl)-4-methoxymethyl-4-piperidinyl]methoxyacetamide N-(2-fluorophenyl)-N-[1-(2-(2-methyl-5-nitroimidazol-1-yl)ethyl)-4-methoxymethyl-4-piperidinyl]-methoxyacetamide N-(phenyl)-N-[1-(2-(1H-pyrazol-1-yl)ethyl)-4-methoxycarbonyl-4-piperidinyl]acrylamide N-(2-methoxyphenyl)-N-[1-(2-(1H-pyrazol-1-yl)ethyl)-4-methoxycarbonyl-4-piperidinyl]propanamide N-(2-fluorophenyl)-N-[1-(2-(N-phthalimidyl)-ethyl)-4-methoxymethyl-4-piperidinyl]propanamide N-(2-fluorophenyl)-N-[1-(2-(3-ethylbenzimid-azol-1-yl)ethyl)-4-methoxymethyl-4-piperidinyl]-propanamide N-(2-fluorophenyl)-N-[1-(2-(1H-pyrazol-1-yl)ethyl)-4-methoxymethyl-4-piperidinyl]methoxyacetamide N-(2-fluorophenyl)-N-[1-(2-(N-phthalimidyl)-ethyl)-4-methoxymethyl-4-piperidinyl]methoxyacetamide N-(2-methoxyphenyl)-N-[1-(2-(N-phthalimidyl)-ethyl)-4-methoxycarbonyl-4-piperidinyl]propanamide N-(2-methoxyphenyl)-N-[1-(2-(3-ethylbenzimid-azol-1-yl)ethyl)-4-methoxycarbonyl-4-piperidinyl]-propanamide N-(2-methoxyphenyl)-N-[1-(2-pyridinylethyl)-4-methoxycarbonyl-4-piperidinyl]propanamide N-(2-methoxyphenyl)-N-[1 (2-(1H-pyrazol-1-yl)-ethyl -4-methoxycarbonyl-4-piperidinyl]methoxyacetamide N-(2-methoxyphenyl)-N-[1-(2-(1H-pyrazol-1-yl)-ethyl)-4-methoxycarbonyl-4-piperidinyl]methoxypropanamide N-(2-methoxyphenyl)-N-[1-(2-(N-phthalimidyl)-ethyl)-4-methoxycarbonyl-4-piperidinyl]methoxypropanamide N-(phenyl)-N-[1-(2-(N-(2,6-dichloroaniline)-imidazol-1-yl)ethyl)-4-methoxycarbonyl-4-piperidinyl]-propanamide N-(phenyl)-N-[1-(2-(N-(2,6-dichloroaniline)-imidazol-1-yl)ethyl)-4-piperidinyl]propanamide N-(2-fluorophenyl)-N-[1-(2-(1H-imidazol-1-yl)ethyl)-4-methoxycarbonyl-4-piperidinyl]propanamide

EXAMPLES 157–172

Further examples of compounds within the scope of the present invention which may be prepared by procedures analogous to those described above include:

trans-N-(2-fluorophenyl)-N-[1-((1H-benzimid-azol-2-yl)methyl)-3-methyl-4-piperidinyl]methoxyacetamide cis-N-(2-fluorophenyl)-N-[1-((1H-benzimidazol-2-yl)methyl)-3-methyl-4-piperidinyl]methoxyacetamide trans-N-(2-fluorophenyl)-N-[1-(2-(2H-tetrazol-2-yl)ethyl)-3-methyl-4-piperidinyl]propanamide trans-N-(2-fluorophenyl)-N-[1-(2-(2H-tetrazol-2-yl)ethyl -3-methyl-4-piperidinyl]methoxyacetamide trans-N-(2-fluorophenyl)-N-[1-(2-(1H-pyrazol-1-yl)ethyl)-3-methyl-4-piperidinyl]methoxyacetamide cis-N-(2-fluorophenyl)-N-[1-(2-(N-phthalimidyl)ethyl)-3-methyl-4-piperidinyl]-methoxyacetamide cis-N-(2-fluorophenyl)-N-[1-(2-(2H-tetrazol-2-yl)ethyl)-3-methyl-4-piperidinyl]propanamide cis-N-(2-fluorophenyl)-N-[1-(2-(2H-tetrazol-2-yl)ethyl)-3-methyl-4-piperidinyl]methoxyacetamide cis-N-(2-fluorophenyl)-N-[1-(2-(3-ethyl-2,3-dihydro-2-oxo-1H-benzimidazol-2-yl)ethyl)-3-methyl-4-piperidinyl]methoxyacetamide trans-N-(2-fluorophenyl)-N-[1-(2-(N-phthalimidyl)ethyl)-3-methyl-4-piperidinyl]propanamide cis-N-(2-fluorophenyl)-N-[1-(2-(1H-pyrazol-1-yl)ethyl)-3-methyl-4-piperidinyl]propanamide trans-N-(2-fluorophenyl)-N-[1-(2-(3-ethyl-2,3-dihydro-2-oxo-1H-benzimidazol-2-yl)ethyl)-3-methyl-4-piperidinyl]propanamide trans-N-(2-fluorophenyl)-N-[1-(2-(1H-pyrazol-1-yl)ethyl)-3-methyl-4-piperidinyl]propanamide cis-N-(2-fluorophenyl)-N-[1-(2-(N-phthalimidyl)ethyl-3-methyl-4 piperidinyl]propanamide cis-N-(2-fluorophenyl)-N-[1-(2-(3-ethyl-2,3-dihydro-2-oxo-1H-benzimidazol-2-yl)ethyl)-3-methyl-4-piperidinyl]propanamide trans-N-(2-fluorophenyl)-N-[1-(2-(3-ethyl-2,3-dihydro-2-oxo-1H-benzimidazol-2-yl)ethyl)-3-methyl-4-piperidinyl]propanamide

EXAMPLE 173

A pharmaceutical composition for parental or intravenous analgesic administration can be prepared from the following ingredients:

| COMPONENTS | AMOUNTS |
| --- | --- |
| N-(phenyl)-N-[1-(2-(1H-pyrrol-1-yl)ethyl)-4-methoxycarbonyl-4-piperidinyl]propanamide | 1 mg |
| isotonic water | 10 liters |

Of course, other compounds of this invention such as those set out in Examples 46-172 may be substituted for N-(phenyl)-N-[1-(2-(1H-pyrrol-1-yl)ethyl)-4-methoxycarbonyl-4-piperidinyl]propanamide with the relative amount of such other compounds in the compositions depending upon their analgesic activity.

EXAMPLE 174

A number of compounds in accordance with the present invention were tested for their analgesic properties. Specifically, the acid addition salts of the compounds, tested in accordance with the invention, were dissolved in sterile water for injection, USP, to form a solution, the concentration of which may vary from 0.00001 mg/ml to 5 mg/ml. The solution was administered intravenously into a mouse tail vain. The ED50 values were obtained from the mouse hot plate analgesia test 58° C. as described in Domer, Floyd R., Animal Experiments in Pharmacological Analysis, Charles C. Thomas, Springfield, 1971, p. 283 ff. The compounds listed in Tables 1 through 4 were tested by this Procedure and found to have the activities listed in the columns on the right side of Tables 1 through 4.

TABLE 1

| COMPOUNDS | M.P. °C. | ED$_{50}$ Mg/Kg |
|---|---|---|
| 1. N-(phenyl)-N-[1-(2-(1H-pyrrol-1-yl)ethyl)-4-methoxycarbonyl-4-piperidinyl]propanamide | 191–192.5 | 0.00084 |
| 2. N-(phenyl)-N-[1-(2-(2-formyl-1H-pyrrol-1-yl)-ethyl)-4-methoxycarbonyl-4-piperidinyl]-propanamide | 175–176 | 0.0026 |
| 3. N-(phenyl)-N-[1-(2-(1H-pyrazol-1-yl)ethyl)-4-methoxycarbonyl-4-piperidinyl]propanamide | 184–187.5 | 0.0094 |
| 4. N-(phenyl)-N-[1-(2-(3-methyl-1H-pyrazol-1-yl)-ethyl)-4-methoxycarbonyl-4-piperidinyl]-propanamide | 170–173 | 0.0038 |
| 5. N-(phenyl)-N-[1-(2-(3,5-dimethyl-1H-pyrazol-1-yl)-ethyl)-4-methoxycarbonyl-4-piperidinyl]-propanamide | 204.5–205.5 | 0.0068 |
| 6. N-(phenyl)-N-[1-(2-(4-iodo-1H-pyrazol-1-yl)ethyl)-4-methoxycarbonyl-4-piperidinyl]propanamide | 163–164.5 | 0.017 |
| 7. N-(phenyl)-N-[1-(2-(3,5-diethoxycarbonyl-1H-pyrazol-1-yl)ethyl)-4-methoxycarbonyl-4-piperidinyl]propanamide | 123–127 | >1 |
| 8. N-(phenyl)-N-[1-(2-(1H-imidazol-1-yl)ethyl)-4-methoxycarbonyl-4-piperidinyl]propanamide | 104–108 | >1 |
| 9. N-(phenyl)-N-[1-(2-(5-nitro-1H-imidazol-1-yl)-ethyl)-4-methoxycarbonyl-4-piperidinyl]-propanamide | 187–188 | >5 |
| 10. N-(phenyl)-N-[1-(2-(2-methyl-5-nitro-1H-imidazol-1-yl)-ethyl)-4-methoxycarbonyl-4-piperidinyl]propanamide | 186.5–188.5 | 0.264 |
| 11. N-(phenyl)-N-[1-(2-(4,5-diethoxycarbonyl-1H-imidazol-1-yl)-ethyl)-4-methoxycarbonyl-4-piperidinyl]propanamide | 152–153 | >5 |
| 12. N-(phenyl)-N-[1-(2-(1H-imidazol-4-yl)ethyl)-4-methoxycarbonyl-4-piperidinyl]propanamide | 139.5–140 | >5 |
| 13. N-(phenyl)-N-[1-(2-(1-methyl-1H-imidazol-2-yl)-ethylthio)-4-methoxycarbonyl-4-piperidinyl]-propanamide | 168–172 | 0.129 |
| 14. N-(phenyl)-N-[1-(2-(1H-triazol-1-yl)ethyl)-4-methoxycarbonyl-4-piperidinyl]propanamide | 171–172 | 1.04 |
| 15. N-(phenyl)-N-[1-(2-(2H-tetrazol-2-yl)ethyl)-4-methoxycarbonyl-4-piperidinyl]propanamide | 198–200 | 0.185 |
| 16. N-(phenyl)-N-[1-(2-(5-phenyl-2H-tetrazol-2-yl)-ethyl)-4-methoxycarbonyl-4-piperidinyl]-propanamide | 130–140 (softens) | >5 |
| 17. N-(phenyl)-N-[1-(2-(1-methyl-1H-tetrazol-5-yl)-ethylthio)-4-methoxycarbonyl-4-piperidinyl]-propanamide | 144–147 | 0.131 |
| 18. N-(phenyl)-N-[1-(2-oxo-2-(2-thienyl)ethyl)-4-methoxycarbonyl-4-piperidinyl]propanamide | 196–199 | 0.0436 |
| 19. N-(phenyl)-N-[1-(2-hydroxy-2-(2-thienyl)ethyl)-4-methoxycarbonyl-4-piperidinyl]propanamide | 179–180 | 0.0018 |
| 20. N-(phenyl)-N-[1-(2-(2,3,4,5-tetrahydro-2-oxo-oxazol-3-yl)ethyl)-4-methoxycarbonyl-4-piperidinyl]propanamide | 160–163 | >1 |
| 21. N-(phenyl)-N-[1-(2-(2,3,4,5-tetrahydro-2-phenyl-5-oxo-1H-pyrazol-1-yl)-ethyl)-4-methoxycarbonyl-4-piperidinyl]propanamide | 163.5–164.5 | 0.502 |
| 22. N-(phenyl)-N-[1-(2-(2,3,4,5-tetrahydro-2,4-dioxo-5-methyl-5-phenyl-1H-imidazol-3-yl)ethyl)-4-methoxycarbonyl-4-piperidinyl]propanamide | 138–141 | >1 |
| 23. N-(phenyl)-N-[1-(2-(5-methylthio-1,3,4-thiadiazol-2-yl)ethylthio)-4-methoxycarbonyl-4-piperidinyl]-propanamide | 144.5–147 | 0.19 |
| 24. N-(phenyl)-N-[1-(2-(2,3-dihydro-2-thioxo-5-phenyl-1,3,4-oxadiazol-3-yl)-ethyl)-4-methoxycarbonyl-4-piperidinyl]propanamide | 140.5–142 | >5 |
| 25. N-(phenyl)-N-[1-(2-(1,2,3,4-tetrahydro-2,4-dioxo-3,3-diethylpyridin-1-yl)-ethyl)-4-methoxycarbonyl-4-piperidinyl]propanamide | 172–174 | 0.156 |
| 26. N-(phenyl)-N-[1-(2-(2,6-dioxo-3-ethyl-3-phenylpiperidin-1-yl)ethyl)-4-methoxycarbonyl-4-piperidinyl]propanamide | 121–124 | 0.462 |
| 27. N-(phenyl)-N-[1-(2-(1,6-dihydro-6-oxo-pyrimidin-1-yl)ethyl)-4-methoxycarbonyl-4-piperidinyl]-propanamide | 182–183 | <1 |
| 28. N-(phenyl)-N-[1-(2-(2-methylthio-1,6-dihydro-4-oxo-5-methylpyrimidin-1-yl)ethyl)-4-methoxycarbonyl-4-piperidinyl]propanamide | 165–166.5 | 0.037 |
| 29. N-(phenyl)-N-[1-(2-(1,2,3,4-tetrahydro-2,4-dioxo-3-ethylpyrimidin-1-yl)-ethyl)-4-methoxycarbonyl-4-piperidinyl]propanamide | 193.5–196 | 2.67 |
| 30. N-(phenyl)-N-[1-(2-(1,6-dihydro-6-oxo-3-methylpyridazin-1-yl)ethyl)-4-methoxycarbonyl-4-piperidinyl]propanamide | 158–160 | 0.051 |

TABLE 1-continued

| COMPOUNDS | M.P. °C. | ED$_{50}$ Mg/Kg |
|---|---|---|
| 31. N-(phenyl)-N-[1-(2-(1,6-dihydro-3-(2-propyl)-6-oxo-1,2,4-triazin-1-yl)-ethyl)-4-methoxycarbonyl-4-piperidinyl]propanamide | 148–152 | 0.621 |
| 32. N-(phenyl)-N-[1-(1H-indol-3-yl(methyl))-4-methoxycarbonyl-4-piperidinyl]propanamide | 188.5–190 | >1 |
| 33. N-(phenyl)-N-[1-(2-(2,3-dihydro-2-oxo-1H-indol-1-yl)ethyl)-4-methoxycarbonyl-4-piperidinyl]propanamide | 166–171 | 0.009 |
| 34. N-(phenyl)-N-[1-(2-(3,3-dimethyl-2,3-dihydro-2-oxo-1H-indol-1-yl)ethyl)-4-methoxycarbonyl-4-piperidinyl]propanamide | 184–185 | 0.038 |
| 35. N-(phenyl)-N-[1-(2-(2,3-dihydro-2-oxo-3,3-spiroethane-1H-indol-1-yl)ethyl)-4-methoxycarbonyl-4-piperidinyl]propanamide | 186.5–190 | 0.022 |
| 36. N-(phenyl)-N-[1-(2-(1,3-dihydro-1,3-dioxo-2H-isoindol-2-yl)-ethyl)-4-methoxycarbonyl-4-piperidinyl]propanamide | 160–163 | 0.19 |
| 37. N-(phenyl)-N-[1-(2H-benzimidazol-1-yl)ethyl))-4-methoxycarbonyl-4-piperidinyl]propanamide | 160–163 | 0.222 |
| 38. N-(phenyl)-N-[1-(0-(1-ethoxycarbonyl-1H-benzopyrazol-3-yl)-ethoxy)-4-methoxycarbonyl-4-piperidinyl]propanamide | 153–155 | >5 |
| 39. N-(phenyl)-N-[1-(2-(3-ethyl-2,3-dihydro-2-oxo-1H-benzimidazol-1-yl)ethyl)-4-methoxycarbonyl-4-piperidinyl]propanamide | 188–190 | 0.121 |
| 40. N-(phenyl)-N-[1-(2-(2,3-dihydro-2-oxo-benzoxazol-3-yl)ethyl)-4-methoxycarbonyl-4-piperidinyl]-propanamide | 134–138 | 0.0303 |
| 41. N-(phenyl)-N-[1-(2-(5-chloro-2,3-dihydro-2-oxo-benzoxazol-3-yl)-ethyl)-4-methoxycarbonyl-4-piperidinyl]propanamide | 180–181 | 0.272 |
| 42. N-(phenyl)-N-[1-(2-oxo-2-(2,3-dihydro-2-oxo-benzoxazol-6-yl)ethyl)-4-methoxycarbonyl-4-piperidinyl]propanamide | 215–217 | >5 |
| 43 N-(phenyl)-N-[1-(7-methoxy-2-oxo-2H-benzopyran-4-yl(methyl))-4-methoxycarbonyl-4-piperidinyl]-propanamide | 184–186 | >5 |
| 44. N-(phenyl)-N-[1-(1,4-benzodioxan-2-yl(methyl))-4-methoxycarbonyl-4-piperidinyl]propanamide | 213.5–214 | 0.0503 |
| 45. N-(phenyl)-N-[1-(2-(2,3-dihydro-3-oxo-4H-1,3-benzothiazin-4-yl)ethyl))-4-methoxycarbonyl-4-piperidinyl]propanamide | 215–218.5 | 0.047 |
| 46. N-(phenyl)-N-[1-(2-(2-methyl-3,4-dihydro-4-oxo-3H-quinazolin-3-yl)ethyl))-4-methoxycarbonyl-4-piperidinyl]propanamide | 210–211 | 0.304 |
| 47. N-(phenyl)-N-[1-(2-(1,2,3,4-tetrahydro-2,4-dioxo-3H-quinazolin-3-yl)ethyl))-4-methoxycarbonyl-4-piperidinyl]propanamide | 190–193 | >1 |
| 48. N-(phenyl)-N-[1-(2-(1-ethyl-1,2,3,4-tetrahydro-2,4-dioxo-3H-quinazolin-3-yl)ethyl))-4-methoxycarbonyl-4-piperidinyl]propanamide | 224–228 | 0.19 |
| 49. N-(phenyl)-N-[1-(2-(1,2,3,6-tetrahydro-1,3-dimethyl-2,6-dioxo-7H-purin-7-yl)ethyl))-4-methoxycarbonyl-4-piperidinyl]propanamide | 194–195 | >5 |
| 50. N-(phenyl)-N-[1-(2-(1,2,3,6-tetrahydro-3,7-dimethyl-2,6-dioxo-1H-purin-1-yl)ethyl))-4-methoxycarbonyl-4-piperidinyl]propanamide | 95 | >5 |
| 51. N-(phenyl)-N-[1-(2-(N-1,8-naphthalenesulfamidyl)-ethyl))-4-methoxycarbonyl-4-piperidinyl]propanamide | 212–214 | 0.223 |
| 52. N-(phenyl)-N-[1-(2-(N-1,8-naphthalene-dicarboxamidyl)ethyl))-4-methoxycarbonyl-4-piperidinyl]propanamide | 140–143 | >1 |
| 53. N-(phenyl)-N-[1-(2-(3-thienyl)ethyl)-4-methoxycarbonyl-4-piperidinyl] propanamide | 192.5–193 | 0.0006 |

TABLE 2

| COMPOUNDS | M.P. °C. | ED$_{50}$ Mg/Kg |
|---|---|---|
| 1. N-(phenyl)-N-[1-(2-(1H-pyrrol-1-yl)ethyl)-4-methoxymethyl-4-piperidinyl]propanamide | 191–196 | 0.0029 |
| 2. N-(phenyl)-N-[1-(2-(2-formyl-1H-pyrrol-1-yl)-ethyl)-4-methoxymethyl-4-piperidinyl]propanamide | 172–175 | 0.0031 |
| 3. N-(phenyl)-N-[1-(2-(1H-pyrazol-1-yl)ethyl)-4-methoxymethyl-4-piperidinyl]propanamide | 169–170 | 0.0155 |
| 4. N-(phenyl)-N-[1-(2-(3,5-dimethyl-1H-pyrazol-1-yl)ethyl)-4-methoxymethyl-4-piperidinyl]propanamide | 167–167.5 | 0.012 |
| 5. N-(phenyl)-N-[1-(2-(4-iodo-1H-pyrazol-1-yl)ethyl)-4-methoxymethyl-4-piperidinyl]propanamide | 184–186 | 0.018 |
| 6. N-(phenyl)-N-[1-(2-(2-methyl-5-nitro-1H-imidazol-1- | 210–202 | 0.262 |

TABLE 2-continued

| COMPOUNDS | M.P. °C. | ED$_{50}$ Mg/Kg |
|---|---|---|
| yl)ethyl)-4-methoxymethyl-4-piperidinyl]propanamide | | |
| 7. N-(phenyl)-N-[1-(2-(1H-imidazol-4-yl)ethyl)-4-methoxymethyl-4-piperidinyl]propanamide | 152-153 | >5 |
| 8. N-(phenyl)-N-[1-(2-(1-methyl-1H-imidazol-2-yl)-ethylthio)-4-methoxymethyl-4-piperidinyl]propanamide | 163.5-164.5 | 0.13 |
| 9. N-(phenyl)-N-[1-(2-(1H-triazol-1-yl)ethyl)-4-methoxymethyl-4-piperidinyl]propanamide | 132.5-134.5 | <1 |
| 10. N-(phenyl)-N-[1-(2-(5-trifluoromethyl-4-methyl-4H-triazol-3-yl)-ethylthio)-4-methoxymethyl-4-piperidinyl]propanamide | 171.5-173.5 | >1 |
| 11. N-(phenyl)-N-[1-(2-(2H-tetrazol-2-yl)ethyl)-4-methoxymethyl-4-piperidinyl]propanamide | 193 | 0.342 |
| 12. N-(phenyl)-N-[1-(2-(5-morpholinyl-2H-tetrazol-2-yl)-ethyl)-4-methoxymethyl-4-piperidinyl]propanamide | 153-154 | >5 |
| 13. N-(phenyl)-N-[1-(1-methyl-2-oxo-2-(2-thienyl)ethyl)-4-methoxymethyl-4-piperidinyl]propanamide | 74 | >1 |
| 14. N-(phenyl)-N-[1-(2-hydroxy-2-(2-thienyl)ethyl)-4-methoxymethyl-4-piperidinyl]8c propanamide | 169-170.5 | 0.005 |
| 15. N-(phenyl)-N-[1-(1-methyl-2-hydroxy-2-(2-thienyl)-ethyl)-4-methoxymethyl-4-piperidinyl]propanamide | 171-174 | 0.015 |
| 16. N-(phenyl)-N-[1-(2-hydroxy-2-(2-furanyl)ethyl)-4-methoxymethyl-4-piperidinyl]propanamide | 175-177 | 0.0034 |
| 17. N-(phenyl)-N-[1-(2-hydroxy-2-(5-methyl-2-furanyl)-ethyl)-4-methoxymethyl-4-piperidinyl]propanamide | 150-156 | 0.0092 |
| 18. N-(phenyl)-N-[1-(2-(3-ethyl-2,3-dihydro-2-oxo-1H-imidazol-1-yl)-ethyl)-4-methoxymethyl-4-piperidinyl]-propanamide | 122-124 | 0.088 |
| 19. N-(phenyl)-N-[1-(2-(2,3,4,5-tetrahydro-2-phenyl-5-oxo-1H-pyrazol-1-yl)-ethyl)-4-methoxymethyl-4-piperidinyl]propanamide | 86-89 | >1 |
| 20. N-(phenyl)-N-[1-(2-(1,5-dihydro-3-methyl-4-amino-5-oxo-1H-triazol-1-yl)-ethyl)-4-methoxymethyl-4-piperidinyl]propanamide | 95 | >5 |
| 21. N-(phenyl)-N-[1-(2-(1,2,3,4-tetrahydro-2,4-dioxo-3,3-diethylpyridin-1-yl)-ethyl)-4-methoxymethyl-4-piperidinyl]propanamide | 159-161.5 | 0.176 |
| 22. N-(phenyl)-N-[1-(2-(2-methylthio-1,6-dihydro-4-oxo-5-methylpyrimidin-1-yl)ethyl)-4-methoxymethyl-4-piperidinyl]propanamide | 168.5-169.5 | 0.055 |
| 23. N-(phenyl)-N-[1-(2-(1,2,3,4-tetrahydro-2,4-dioxo-3-ethylpyrimidin-1-yl)-ethyl)-4-methoxymethyl-4-piperidinyl]propanamide | 158-160 | 0.602 |
| 24. N-(phenyl)-N-[1-(2-(2,3-dihydro-2-oxo-1H-indol-1-yl)-ethyl)-4-methoxymethyl-4-piperidinyl]propanamide | 108.5-112 | 0.0027 |
| 25. N-(phenyl)-N-[1-(2-(3,3-dimethyl-2,3-dihydro-2-oxo-1H-indol-1-yl)ethyl)-4-methoxymethyl-4-piperidinyl]propanamide | 186.5-190 | 0.027 |
| 26. N-(phenyl)-N-[1-(2-(2,3-dihydro-2-oxo-3,3-spiroethane-1H-indol-1-yl)ethyl)-4-methoxymethyl-4-piperidinyl]propanamide | 194.5-196.5 | 0.064 |
| 27. N-(phenyl)-N-[1-(2-(1,3-dihydro-1-oxo-2H-isoindol-2-yl)ethyl)-4-methoxymethyl-4-piperidinyl]propanamide | 160-163 | 1.5 |
| 28. N-(phenyl)-N-[1-(2-(1,3-dihydro-1,3-dioxo-2H-isoindol-2-yl)-ethyl)-4-methoxymethyl-4-piperidinyl]propanamide | 172.5-174.5 | 0.799 |
| 29. N-(phenyl)-N-[1-(2-(3-ethyl-2,3-dihydro-2-oxo-1H-benzimidazol-1-yl)ethyl)-4-methoxymethyl-4-piperidinyl]propanamide | 191.5-192.5 | 0.092 |
| 30. N-(phenyl)-N-[1-(2-(2,3-dihydro-2-oxo-benzoxazol-3-yl)ethyl)-4-methoxymethyl-4-piperidinyl]propanamide | 194-195 | 0.10 |
| 31. N-(phenyl)-N-[1-(2-(2-oxo-2H-benzopyran-7-oxy)ethyl)-4-methoxymethyl-4-piperidinyl]propanamide | 110-113 | >5 |
| 32. N-(phenyl)-N-[1-(1,4-benzodioxan-2-yl(methyl))-4-methoxymethyl-4-piperidinyl]propanamide | 200-202 | 0.10 |
| 33. N-(phenyl)-N-[1-(6-fluoro-1,3-benzodioxan-8-yl(methyl))-4-methoxymethyl-4-piperidinyl]-propanamide | 196-197 | >1 |
| 34. N-(phenyl)-N-[1-(2-(2-methyl-3,4-dihydro-4-oxo-3H-quinazolin-3-yl)ethyl))-4-methoxymethyl-4-piperidinyl]propanamide | 214.5-216.5 | 0.424 |
| 35. N-(phenyl)-N-[1-(2-(1-ethyl-1,2,3,4-tetrahydro-2,4-dioxo-3H-quinazolin-3-yl)ethyl))-4-methoxymethyl-4-piperidinyl]propanamide | 189-190 | 0.148 |
| 36. N-(phenyl)-N-[1-(2-(N-1,8-naphthalenecarboxamidyl)-ethyl))-4-methoxymethyl-4-piperidinyl]propanamide | 95 | 0.496 |
| 37. N-(phenyl)-N-[1-(2-(3-thienyl)ethyl)-4-methoxymethyl-4-piperidinyl]propanamide | 177-179 | 0.0038 |

TABLE 3

| | COMPOUNDS | M.P. °C. | ED$_{50}$ Mg/Kg |
|---|---|---|---|
| 1. | N-(2-fluorophenyl)-N-[1-(2-(1H-pyrazol-1-yl)-ethyl)-4-methoxycarbonyl-4-piperidinyl)]-propanamide | 186–188 | 0.0021 |
| 2. | N-(2-fluorophenyl)-N-[1-(2-(N-phthalimidyl)-ethyl)-4-methoxycarbonyl-4-piperidinyl]-propanamide | 150–154 | 0.196 |
| 3. | N-(2-fluorophenyl)-N-[1-(2-(N-phthalimidyl)-ethyl)-4-methoxycarbonyl-4-piperidinyl]-2-methoxypropanamide | 135–140 | 1.5 |
| 4. | N-(2-fluorophenyl)-N-[1-(2-(1H-pyrazol-1-yl)-ethyl)-4-methoxymethyl-4-piperidinyl]-propanamide | 172–173 | 0.016 |
| 5. | N-(2-fluorophenyl)-N-[1-(2-(3-ethylbenzimidazol-1-yl)ethyl)-4-methoxymethyl-4-piperidinyl]-methoxyacetamide | 168–169 | 0.367 |
| 6. | N-(2-fluorophenyl)-N-[1-(2-(2-methyl-5-nitroimidazol-1-yl)ethyl)-4-methoxymethyl-4-piperidinyl]methoxyacetamide | 145–148 | 0.937 |
| 7. | N-(phenyl)-N-[1-(2-(1H-pyrazol-1-yl)ethyl)-4-methoxycarbonyl-4-piperidinyl]acrylamide | 208 | 0.012 |
| 8. | N-(2-methoxyphenyl)-N-[1-(2-(1H-pyrazol-1-yl)-ethyl)-4-methoxycarbonyl-4-piperidinyl]-propanamide | 193–195 | 0.026 |
| 9. | N-(2-fluorophenyl)-N-[1-(2-(N-phthalimidyl)-ethyl)-4-methoxymethyl-4-piperidinyl]-propanamide | 165–167 | 0.683 |
| 10. | N-(2-fluorophenyl)-N-[1-(2-(3-ethylbenzimidazol-1-yl)ethyl)-4-methoxymethyl-4-piperidinyl]-propanamide | 182–183 | 0.12 |
| 11. | N-(2-fluorophenyl)-N-[1-(2-(1H-pyrazol-1-yl)-ethyl)-4-methoxymethyl-4-piperidinyl]-methoxyacetamide | 161–163 | 0.12 |
| 12. | N-(2-fluorophenyl)-N-[1-(2-(N-phthalimidyl)-ethyl)-4-methoxymethyl-4-piperidinyl]-methoxyacetamide | 130–135 | 0.468 |
| 13. | N-(2-methoxyphenyl)-N-[1-(2-(N-phthalimidyl)-ethyl)-4-methoxycarbonyl-4-piperidinyl]-propanamide | 163–166 | 0.106 |
| 14. | N-(2-methoxyphenyl)-N-[1-(2-(3-ethylbenzimidazol-1-yl)ethyl)-4-methoxycarbonyl-4-piperidinyl]-propanamide | 166–168 | 0.094 |
| 15. | N-(2-methoxyphenyl-N-[1-(2-pyridinylethyl)-4-methoxycarbonyl-4-piperidinyl]propanamide | 155–158 | 0.020 |
| 16. | N-(2-methoxyphenyl)-N-[1-(2-(1H-pyrazol-1-yl)-ethyl)-4-methoxycarbonyl-4-piperidinyl]-methoxyacetamide | 172–173 | 0.309 |
| 17. | N-(2-methoxyphenyl)-N-[1-(2-(1H-pyrazol-1-yl)-ethyl)-4-methoxycarbonyl-4-piperidinyl]-methoxypropanamide | 190–192 | 0.149 |
| 18. | N-(2-methoxyphenyl)-N-[1-(2-(N-phthalimidyl)-ethyl)-4-methoxycarbonyl-4-piperidinyl]-methoxypropanamide | 174–175 | 0.389 |
| 19. | N-(phenyl)-N-[1-(2-(N-(2,6-dichloroaniline)-imidazol-1-yl)ethyl)-4-methoxycarbonyl-4-piperidinyl]propanamide | 103 | 2 |
| 20. | N-(2-fluorophenyl)-N-[1-(2-(2-methyl-1H-imidazol-1-yl)ethyl)-4-methoxycarbonyl-4-piperidinyl]-propanamide | 92 | 5 |
| 21. | N-(2-fluorophenyl)-N-[1-(2-(1H-imidazol-1-yl)-ethyl)-4-methoxycarbonyl-4-piperidinyl]propanamide | 120 | 0.171 |

TABLE 4

| | COMPOUNDS | M.P. °C. | ED$_{50}$ Mg/Kg |
|---|---|---|---|
| 1. | trans-N-(2-fluorophenyl)-N-[1-((1H-benzimidazol-2-yl)methyl)-3-methyl-4-piperidinyl]-methoxyacetamide | 134–136 | >5 |
| 2. | cis-N-(2-fluorophenyl)-N-[1-((1H-benzimidazol-2-yl)methyl)-3-methyl-4-piperidinyl]-methoxyacetamide | 144–145 | >5 |
| 3. | trans-N-(2-fluorophenyl)-N-[1-(2-(2H-tetrazol-2-yl)ethyl)-3-methyl-4-piperidinyl]propanamide | 160–161 | 2.5 |
| 4. | trans-N-(2-fluorophenyl)-N-[1-(2-(2H-tetrazol-2-yl)ethyl)-3-methyl-4-piperidinyl]methoxyacetamide | 177–178 | 6.0 |
| 5. | trans-N-(2-fluorophenyl)-N-[1-(2-(1H-pyrazol-1-yl)ethyl)-3-methyl-4-piperidinyl]methoxyacetamide | 135–136 | 2.5 |
| 6. | cis-N-(2-fluorophenyl)-N-[1-(2-(N-phthalimidyl)-ethyl)-3-methyl-4-piperidinyl]methoxyacetamide | 124–126 | 0.5 |
| 7. | cis-N-(2-fluorophenyl)-N-[1-(2-(2H-tetrazol-2- | 96–97 | 0.174 |

TABLE 4-continued

| | COMPOUNDS | M.P. °C. | ED$_{50}$ Mg/Kg |
|---|---|---|---|
| 8. | yl)ethyl)-3-methyl-4-piperidinyl]propanamide cis-N-(2-fluorophenyl)-N-[1-(2-(2H-tetrazol-2-yl)ethyl)-3-methyl-4-piperidinyl]methoxyacetamide | 117–118 | 0.329 |
| 9. | cis-N-(2-fluorophenyl)-N-[1-(2-(3-ethyl-2,3-dihydro-2-oxo-1H-benzimidazol-2-yl)ethyl)-3-methyl-4-piperidinyl]methoxyacetamide | 182–183 | 0.0058 |
| 10. | trans-N-(2-fluorophenyl)-N-[1-(2-N-phthalimidyl)-ethyl)-3-methyl-4-piperidinyl]propanamide | 163–164 | 1.8 |
| 11. | cis-N-(2-fluorophenyl)-N-[1-(2-(1H-pyrazol-1-yl)-ethyl)-3-methyl-4-piperidinyl]propanamide | 114–115 | 0.0015 |
| 12. | trans-N-(2-fluorophenyl)-N-[1-(2-(3-ethyl-2,3-dihyro-2-oxo-1H-benzimidazol-2-yl)ethyl)-3-methyl-4-piperidinyl]propanamide | 186–187 | 0.085 |
| 13. | trans-N-(2-fluorophenyl)-N-[1-(2-(1H-pyrazol-1-yl)ethyl)-3-methyl-4-piperidinyl]propanamide | 157–158 | 0.044 |
| 14. | cis-N-(2-fluorophenyl)-N-[1-(2-(N-phthalimidyl)-ethyl)-3-methyl-4-piperidinyl] propanamide | 153–154 | 0.275 |
| 15. | cis-N-(2-fluorophenyl)-N-[1-(2-(3-ethyl-2,3-dihyro-2-oxo-1H-benzimidazol-2-yl)ethyl)-3-methyl-4-piperidinyl]propanamide | 175–176 | 0.0174 |
| 16. | trans-N-(2-fluorophenyl)-N-[1-(2-(3-ethyl-2,3-dihyro-2-oxo-1H-benzimidazol-2-yl)ethyl)-3-methyl-4-piperidinyl]propanamide | 154–155 | >5 |

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A compound having the formula:

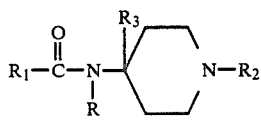

optically active isometric forms thereof, and pharmaceutically acceptable acid addition salts thereof, wherein:

R is selected from the group consisting of phenyl and substituted phenyl, wherein said substituents are members independently selected from the group consisting one or more of halogen;

$R_1$ is selected form the group consisting of lower alkyl, lower-alkenyl, and a lower-alkoxy lower-alkyl group having from 2 to 6 carbon atoms;

$R_2$ is a quniazolyl lower-alkyl group or a purinyl lower-alkyl group, the lower-alkyl portion of said groups containing from 1 to 7 carbon atoms and the heterocyclic portion thereof being unsubstituted or substituted with one or more substituents selected from the group consisting of halogen, hydroxyl, nitro, amino, lower-alkoxy carbonyl, lower-alkyl, lower-cycloalkyl, lower alkoxy, halogenated lower-alkyl, aryl and halogenated aryl; and $R_3$ is lower-alkoxy carbonyl or lower-alkoxy methyl.

2. A compound according to claim 1, wherein R is selected from the group consisting of phenyl, 2-fluorophenyl and 2-methoxyphenyl.

3. A compound according to claim 1, wherein $R_1$ is selected from the group consisting of ethyl, ethenyl, methoxymethyl and 1-methoxyethyl.

4. A compound according to claim 1, wherein $R_2$ is selected from the group consisting of substituted or unsubstituted quinazolin-3-yl lower-alkyl, purin-1-yl lower-alkyl and purin-7-yl lower-alkyl groups.

5. A compound according to claim 1, wherein $R_3$ is methoxy carbonyl or methoxymethyl.

6. A compound according to claim 1, wherein R is a phenyl group;

$R_2$ is a substituted or unsubstituted lower-alkyl group or purinyl lower-alkyl group; and $R_3$ is a lower-alkoxy carbonyl group.

7. A compound according to claim 6, wherein $R_1$ is ethyl.

8. A compound according to claim 6, wherein $R_2$ is selected from the group consisting of substituted or unsubstituted quinazolin-3-yl lower-alkyl, purin-1-yl lower-alkyl and purin-7-yl lower alkyl groups.

9. A compound according to claim 1, wherein R is a phenyl group;

$R_2$ is a substituted or unsubstituted quinazolinyl lower-alkyl group or purinyl lower-alkyl group; and $R_3$ is a lower-alkoxy methyl group.

10. A compound according to claim 9, wherein $R_1$ is ethyl and $R_3$ is methoxymethyl.

11. A compound in accordance with claim 6, which comprises N-(phenyl)-N-[1-(2-(1,2,3,6-tetrahydro-1,3-dimethyl-2,6-dioxo-7H-purin-7-yl)ethyl))-4-methoxycarbonyl-4-piperidinyl]propanamide or a pharmaceutically acceptable acid addition salt thereof.

12. A compound in accordance with claim 6, which comprises N-(phenyl)-N-[1-(2-(2-methyl-3,4-dihydro-4-oxo-3H-quinazolin-3-yl)ethyl)-4-methoxymethyl-4-piperidinyl]propanamide or a pharmaceutically acceptable acid addition salt thereof.

13. A compound according to claim 9, wherein $R_2$ is selected from the group consisting of substituted or unsubstituted quinazolin-3-yl lower alkyl, purin-1-yl lower-alkyl and purin-7-yl lower-alkyl groups.

14. An analgesic composition comprising a non-toxic pharmaceutically acceptable carrier and an analgesically effective amount of a compound as defined in claim 1.

15. The composition according to claim 14, wherein R is selected from the group consisting of phenyl, 2-fluorophenyl and 2-methoxyphenyl.

16. The composition according to claim 14, wherein $R_1$ is selected from the group consisting of ethyl, ethenyl, methoxymethyl and 1-methoxyethyl.

17. A composition according to claim 14, wherein $R_2$ is selected from the group consisting of substituted or unsubstituted quinazolinyl-3-yl lower-alkyl, purin-1-yl, lower-alkyl and purin-7-yl lower-alkyl groups.

18. A composition according to claim 14, wherein $R_3$ is methoxy carbonyl or methoxymethyl.

19. A composition according to claim 14, wherein R is a phenyl group;
   $R_2$ is substituted or unsubstituted quinazolinyl lower-alkyl group or purinyl lower-alkyl group; and
   $R_3$ is lower-alkoxy carbonyl group.

20. A composition according to claim 19, wherein $R_1$ is ethyl.

21. A composition according to claim 19, wherein $R_3$ is methoxy carbonyl.

22. A composition according to claim 19, wherein $R_2$ is selected from the group consisting of substituted or unsubstituted quinazolin-3-yl lower-alkyl, purin-1-yl lower-alkyl and purin-7-yl lower-alkyl groups.

23. A composition in accordance with claim 14, wherein the compound comprises N-(phenyl)-N-[1-(2-(1,2,3,6-tetrahydro-1,3-dimethyl-2,6-dioxo-7H-purin-7-yl)ethyl))-4-methoxy-carbonyl-4-piperidinyl]propanamide or a pharmaceutically acceptable acid addition salt thereof.

24. A composition in accordance with claim 14, wherein the compound comprises N-(phenyl)-N-[1-(2-(2-methyl-3,4-dihydro-4-oxo-3H-quinazolin-3-yl)ethyl))-4-methoxymethyl-4-piperidinyl]propanamide or a pharmaceutically acceptable acid addition salt thereof.

25. A method for producing analgesia in a mammal in need thereof comprising administering to the mammal an analgesically effective amount of a compound as defined in claim 1.

26. A method according to claim 25, wherein R is selected from the group consisting of phenyl, 2-fluorophenyl and 2-methoxyphenyl.

27. A method according to claim 25, wherein $R_1$ is selected from the group consisting of ethyl, ethenyl, methoxymethyl and 1-methoxyethyl.

28. A method according to claim 25, wherein R is a phenyl group;
   $R_2$ is selected from the group consisting of substituted or unsubstituted quinazolinyl lower-alkyl and purinyl lower-alkyl groups; and
   $R_3$ is a lower-alkoxy carbonyl group.

29. A method according to claim 25, wherein $R_2$ is selected from the group consisting of substituted or unsubstituted quinazolin-3-yl lower-alkyl, purin-1-yl lower-alkyl and purin-7-yl lower-alkyl.

30. A method according to claim 28, wherein $R_2$ is selected from the group consisting of substituted or unsubstituted quinazolin-3-yl lower-alkyl, purin-1-yl lower-alkyl and purin-7-yl lower-alkyl groups.

* * * * *

UNITED STATES PATENT AND TRADEMARK OFFICE
CERTIFICATE OF CORRECTION

PATENT NO. : 5,053,411
DATED : October 1, 1991
INVENTOR(S) : Bagley, et al

It is certified that error appears in the above-indentified patent and that said Letters Patent is hereby corrected as shown below:

Col. 29, line 30, delete "23", and insert -- 29 --.

Col. 47, Claim 1, line 47, after "halogen", insert -- and lower alkoxy -- .

Signed and Sealed this

Twenty-ninth Day of June, 1993

Attest:

MICHAEL K. KIRK

*Attesting Officer*   Acting Commissioner of Patents and Trademarks